United States Patent [19]

Theodoridis

[11] Patent Number: 5,084,085
[45] Date of Patent: Jan. 28, 1992

[54] HERBICIDAL ARYLOXYPHENYLTRIAZOLINONES AND RELATED COMPOUNDS

[75] Inventor: George Theodoridis, Princeton, N.J.

[73] Assignee: FMC Corporation, Philadelphia, Pa.

[21] Appl. No.: 562,544

[22] Filed: Aug. 3, 1990

Related U.S. Application Data

[63] Continuation-in-part of Ser. No. 449,091, Dec. 8, 1989, abandoned, which is a continuation-in-part of Ser. No. 161,348, Feb. 19, 1988, abandoned, which is a continuation-in-part of Ser. No. 898,453, Aug. 20, 1986, abandoned.

[51] Int. Cl.$^5$ .................. A01N 43/653; C07D 249/12
[52] U.S. Cl. ..................... 71/92; 548/263.2; 548/263.4; 548/263.8
[58] Field of Search .............. 71/92; 548/263.2, 263.4, 548/263.8

[56] References Cited

U.S. PATENT DOCUMENTS

| | | | |
|---|---|---|---|
| 4,702,763 | 10/1987 | Maravetz | 71/90 |
| 4,818,276 | 4/1989 | Maravetz et al. | 71/92 |
| 4,919,708 | 4/1990 | Maravetz | 71/92 |

FOREIGN PATENT DOCUMENTS 2725148 12/1978 Fed. Rep. of Germany .......... 71/92
78/3182 6/1977 South Africa .

Primary Examiner—Patricia L. Morris
Attorney, Agent, or Firm—Norman L. Craig; Robert M. Kennedy; H. Robinson Ertelt

[57] ABSTRACT

Herbicidal aryloxyphenyltriazolinones compounds which are ring-substituted aryloxyphenyltriazolinones, such as compounds of the formula

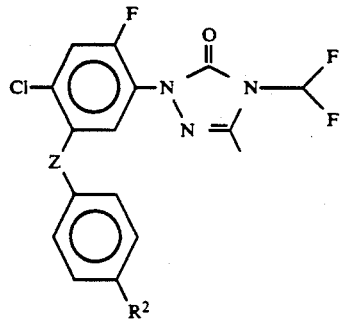

where Z is O, S, NH, or alkylamino; and where $R^2$ is, for instance, $C_2H_5OCO-CH(CH_3)-O-$ or $CH_3SO_2-NH-CO-CH(CH_3)-O-$.

22 Claims, No Drawings

HERBICIDAL ARYLOXYPHENYLTRIAZOLINONES AND RELATED COMPOUNDS

This application is a continuation-in-part of application Ser. No. 449,091 filed Dec. 8, 1989 which is a continuation-in-part of application Ser. No. 161,348 filed Feb. 19, 1988 now abandoned which is a continuation-in-part of application Ser. No. 898,453 filed Aug. 20, 1986 now abandoned.

This invention relates to novel herbicides for weed control in agriculture, horticulture and other fields where it is desired to control unwanted plant growth, such as grassy or broadleaf plant species. The information also relates to intermediates for the production of such herbicides.

A particularly effective aspect of this invention relates to herbicidal compounds of the formula

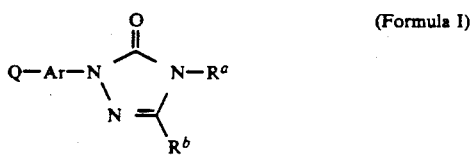
(Formula I)

where Q—Ar— is a substituted phenyl radical (e.g. of the formula

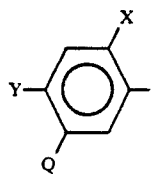

in which the substituent Q is at the 5-position (meta to the nitrogen of said formula I); Q is

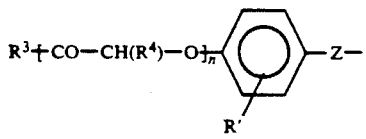

or

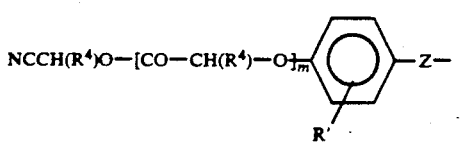

Z may be O, S, NH or alkylamino (such as lower alkylamino, e.g. methylamino).

$R^4$ may be H or $CH_3$; and $R^3$ may be OH, O$^-$ak$^+$, alkoxy (e.g. lower alkoxy such as methoxy or ethoxy), cycloalkyloxy, lower alkenyloxy or alkynyloxy (e.g. allyloxy or propargyloxy), —O[CHR$^8$(CH$_2$)$_p$O]$_r$R$^9$, amino, arylamino (e.g. phenylamino), alkylamino (e.g. lower alkylamino such as methylamino or dimethylamino), alkenylamino (e.g. diallylamino), alkoxyamino (e.g. lower alkoxyamino such as methoxyamino) or alkyl-, haloalkyl- or a arylsulfonylamino of the formula —N(alkyl)SO$_2$R$^5$, —NHSO$_2$R$^5$ or —N(SO$_2$R$^5$)SO$_2$R$^6$.

$R^5$ and $R^6$ may be independently alkyl (e.g. lower alkyl such as methyl, ethyl or propyl), haloalkyl (e.g. halo lower alkyl such as trifluoromethyl) or aryl such as phenyl or substituted phenyl, (e.g. alkoxy-substituted and/or halo-substituted phenyl).

n may be 1 or 2, m may be zero or 1, p may be 0 to 5, and r may be 1 to 6, preferably 1 to 3.

ak$^+$ is a salt forming group such as sodium, potassium or ammonium.

$R^8$ is H or $CH_3$; and p is 0 to 5; with the identity of $R^8$ and the value of p being independently variable within an $R^3$ radical (e.g. $R^3$=O[CH(R$^8$=CH$_3$)(CH$_2$)$_{p=1}$O][CH(R$^8$=H)(CH$_2$)$_{p=3}$O]R$^9$);

$R^9$ is alkyl.

R' may be H, alkyl (e.g. lower alkyl such as methyl), halogen such as Cl, Br or F, haloalkyl (e.g. lower haloalkyl such as CF$_3$, CH$_2$F or CHF$_2$), nitro, NH$_2$, lower alkoxy or alkylthio (e.g. OCH$_3$ or SCH$_3$) or cyano. There may be a plurality of R' substituents on the same benzene ring.

In Formula I above, Ar, R$^a$ and R$^b$ are so chosen that when Q is methoxy or propargyloxy (instead of Q having the formula given above) the compound is a herbicide. Compounds in which Q in Formula I is methoxy or propargyloxy are, for convenience, here designated as the Methoxy Analogs and the Propargyloxy Analogs of the claimed novel compounds. Such Methoxy Analogs and Propargyloxy Analogs are well known in the art. For instance, the Methoxy Analog of Compounds 1–7, 26–72 and 88–91 of this application (see Table I below) is the compound 1-(4-chloro-2-fluoro-5-methoxyphenyl)-3-methyl-4-difluoromethyl-Δ$^2$-1,2,4-triazolin-5-one of Example 1D of International Application WO 85/04307 published Oct. 10, 1985 (U.S. Pat. No. 4,818,276), and the Propargyloxy Analog of said numbered compounds 1–7, 26–72 and 88–91 is the compound of Example 2 of that same International Application, while the Methoxy and Propargyloxy Analogs of compounds 82 and 92 are described in U.S. Pat. No. 4,398,943.

The substituents R$^a$ and R$^b$ on the triazolinone ring may be any of those known in the art. For instance, each may, independently, be lower alkyl or lower haloalkyl (e.g. fluoroalkyl). Additionally R$^a$ may be alkenyl or alkynyl; and R$^b$ may be hydrogen, halogen, alkylsulfonyl, alkylthio, alkoxy, or haloalkylsulfonyl Some examples of R$^a$ an R$^b$ substituents are found in Table 1.

R$^a$ is preferably lower haloalkyl such as a fluoroalkyl, e.g. CF$_2$CHF$_2$, particularly CHF$_2$.

R$^b$ is preferably lower alkyl, e.g. CH$_3$.

Preferably, "Ar" carries a substituent (i.e. other than H) at the 2-position or the 4-position of the phenyl radical, most preferably at both the 2- and 4-positions.

X may be H, halogen such as Cl, Br or F (preferably Cl or F), alkyl (e.g. lower alkyl such as methyl), haloalkyl (e.g. lower haloalkyl such as CF$_3$, CH$_2$F or CHF$_2$) or nitro; and Y may be H, halogen such as Cl, Br or F (preferably Cl), alkyl (e.g. lower alkyl such as methyl), alkoxy (e.g. lower alkoxy such as methoxy), alkylthio (e.g. lower alkylthio such as methylthio), haloalkyl (e.g. lower haloalkyl such as fluoroalkyl), nitro, cyano, alkylsulfonyl alkyl, -SOCF$_3$ or halo lower alkoxy such as —OCHF$_2$. Presently preferred X, Y substituents are: 2-F, 4-Cl; 2-F, 4-Br; 2,4-Cl$_2$; 2-Br, 4-Cl; and 2-F, 4-CF$_3$, particularly 2-F, 4-Cl and 2,4-Cl$_2$.

A broader aspect of the invention relates to herbicidal compounds of the formula

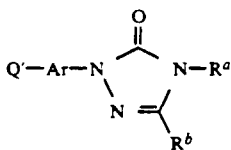

in which Q' (which generically includes Q) is:

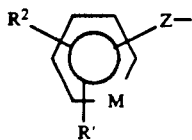

in which $R^2$ may be H, halogen (such as Cl, Br or F), hydroxy, alkylcarbonyloxy (such as lower alkylcarbonyloxy, e.g. acetoxy), alkenyloxy (such as lower alkenyloxy, e.g. allyloxy), alkynyloxy (such as lower alkynyloxy, e.g. propargyloxy), alkyl (such as lower alkyl, e.g. methyl), haloalkyl (such as halo lower alkyl, e.g. $CF_3$, $CHF_2$, $C_2F_5$ or $CH_2F$), alkoxy (such as lower alkoxy, e.g. methoxy), haloalkoxy (such as halo lower alkoxy, e.g. $OCHF_2$ and $OCF_3$), nitro, amino, cyano, alkylthio (such as lower alkylthio e.g. methylthio), —COOH, $COOR^7$, —$CONHSO_2R^5$, —$CONH_2$, —$CONHR^5$, —$CONHOR^7$ (where $R^7$ is lower alkyl such as methyl), —$COOCH(R^4)COR^3$, -$NHSO_2R^7$, —$N(SO_2R^7)_2$, —$SCH(R^4)COR^3$ or —$NHCH(R^4)COR^3$ or $R^3[CO—CH(R^4)—O]_n$- or $NCCH(R^4)O—[COCH(R^4)—O]_m$—, and M is CH or N. $R_7$ is lower alkyl.

Z, m, n, r, p, R', $R^3$, $R^4$, $R^5$, $R^6$, $R^8$ and $R^9$ (as well as Ar, $R^a$, $R^b$, X and Y) are as described earlier. Of particular interest are those compounds in which $R^3$ is —$O[CH_2(CH_2)_pO]_rCH_3$. Ar, $R^a$ and $R^b$ are so chosen that the Methoxy Analog or Propargyloxy Analog (in which Q' is methoxy or propargyloxy instead of the Q' described above) is a herbicide.

In this application it is preferable that any alkyl, alkenyl, or alkynyl moiety (e.g., the hydrocarbon chain of an alkyl, haloalkyl, alkoxy, or alkylthio substituent) have up to 6 carbon atoms, and any cycloalkyl have from 3 to 7 carbon atoms.

In the preferred compounds of this invention, $R^a$ and $R^b$ and Ar (or X and Y) are so chosen that the Methoxy Analog or the Propargyloxy Analog of such preferred compound has marked herbicidal properties, such Analog showing at least 50% kill of at least one of the following modes at the rate of 0.5 kg/ha, and more preferably showing such 50% kill when applied at the rate of 0.1 kg/ha:

Species: velvetleaf (*Abutilon theophrasti*), green foxtail (*Setaria viridis*); Modes: pre-emergent, post-emergent. Testing for such herbicidal activity may be carried out in the manner described below (under the heading "Herbicidal Activity").

Representative compounds of this invention (including certain intermediates) are listed in Tables 1, 1A, 1B and 1C.

The compounds of this invention may be prepared by the use of steps generally described in the literature or by methods analogous or similar thereto and within the skill of the art. In Examples 1-7 below, the starting material is the Hydroxy Analog of the compound (which Hydroxy Analog may be obtained by treatment of the corresponding Methoxy Analog as described in Example 1E of published International Application WO 85/04307). In Examples 1-4, 6, 7 the Hydroxy Analog is treated to form the nitrophenyl (or nitropyridinyl) ether, which is then treated to form the hydroxyphenyl (or hydroxypyridinyl) ether, followed by etherification with the appropriate moiety. In Example 5, the Hydroxy Analog is treated to form the cyanophenyl ether after which the cyano group is converted to the desired substituent, in that case eventually an N-alkylsulfonylaminocarbonyl substituent. Other methods are illustrated below. In Method B the process is illustrated with a compound in which "M" is N instead of CH; in that method the hydroxypyridiyl ether is produced by treating the methoxypyridyl ether with $BBr_3$. In Method C the first step is an etherification to introduce the $R^2$ group followed by a reduction of the nitro substituent (on the Ar group) to form an amino group which is then converted to a chlorine substituent. Methods D and E relate to processes for making the Q'—Ar—$NH_2$ compound whose $NH_2$ group can then be converted to the final triazolinone moiety in a conventional manner. In Method D the $NH_2$ group has been acylated to protect it during the various reactions. In Method E that $NH_2$ group is introduced by nitration followed by reduction. While these methods are illustrated specifically with reagents chosen to form the product of Example 1 (or, in Method B, the corresponding pyridyl compound), it will be understood by those skilled in the art that analogous reactants may be used to form other compounds disclosed herein.

Method B: React 1-(4-chloro-2-fluoro-5-hydroxyphenyl)-4-difluoromethyl-4,5-dihydro-3-methyl-1,2,4-triazol-5(1H)-one first with sodium hydride (e.g. in N,N-dimethylformamide ["DMF"]) followed by reaction with an appropriately substituted 5-methoxypyridine (e.g. 2-fluoro-or 2-chloro-5-methoxypyridine) to form 1-[4-chloro-2-fluoro-5-(5-methoxypyridin-2-yl)oxyphenyl]-4-difluoromethyl-4,5-dihydro-3-methyl-1,2,4-triazol-5(1H)-one. Then treat with boron tribromide (e.g. in methylene chloride) followed by reaction with an alkyl (e.g. ethyl) 2-bromopropionate (e.g. in the presence of potassium carbonate and acetone) to form the corresponding alkyl 2-[5-[2-chloro-4-fluoro-5-(4-difluoromethyl-4,5-dihydro-3-methyl-5-oxo-1H-1,2,4-triazol-1-yl)phenoxy]-pyridin-2-yl]oxypropionate.

Method C: React 1-(2,5-difluoro-4-nitrophenyl)-4-difluoromethyl-4,5-dihydro-3-methyl-1,2,4-triazol-5(1H)-one with an alkyl (e.g. ethyl) 2-(4-hydroxyphenoxy)-propionate in the presence of a base (such as sodium hydride in N,N-dimethylformamide) to form the alkyl 2-[4-[4-fluoro-2-nitro-5-(4-difluoromethyl-4,5-dihydro-3-methyl-5-oxo-1H-1,2,4-triazol-1-yl)phenoxy]phenoxy]-propionate. Reduce the nitro group by hydrogenation (e.g. in ethanol with a catalytic amount of platinum oxide) to form the alkyl 2-[4-[2-amino-4-fluoro-5-(4-difluoromethyl-4,5-dihydro-3-methyl-5-oxo-1H-1,2,4-triazol-1-yl)phenoxy]phenoxy]propionate. Then treat (as with sodium nitrite and hydrochloric acid, followed by copper (I) chloride) to form the corresponding alkyl 2-[2-chloro-4-fluoro-5-(4-difluoromethyl-4,5-dihydro -3-methyl-5-oxo-1H-1,2,4-triazol-1-yl)phenoxy]phenoxy]-propionate. propionate.

Method D: React 4-chloro-2-fluoro-5-hydroxyacetanilide with 4-fluoronitrobenzene (e.g. by heating in the presence of a base, such as sodium hydride, and DMF) to form 4-chloro-2-fluoro-5-(4-nitrophenoxy)-acetanilide. Reduce the $NO_2$ group (as by hydrogenation in ethanol with a catalytic amount of platinum oxide) to form 5-(4-aminophenoxy)-4-chloro-2-fluoroacetanilide. Treat the latter (e.g. with sodium nitrite and sulfuric acid followed by copper (II) sulfate) to form 4-chloro-2-fluoro-5-(4-hydroxyphenoxy)acetanilide. Then react with an alkyl halide, such as methyl iodide (e.g. in the presence of potassium carbonate and acetone) to form the alkyl 4-chloro-2-fluoro-5-(4-methoxyphenoxy)acetanilide. Hydrolyze the latter (as with hydrochloric acid) to form the corresponding aniline, e.g. 4-chloro-2-fluoro-5-(4-methoxyphenoxy)aniline.

Method E: React 2,5-difluoronitrobenzene with 4-methoxyphenol (e.g. in the presence of a base, such as sodium hydride, and DMF) to form 5-fluoro-2-(4-methoxyphenoxy)nitrobenzene. Reduce the nitro group (as by hydrogenation in ethanol with a catalytic amount of platinum oxide) to form 5-fluoro-2-(4-methoxyphenoxy)-aniline. Nitrate the latter (as with nitric acid and sulfuric acid) to form 5-fluoro-2-(4-methoxyphenoxy)-4-nitroaniline. Treat the latter (e.g. first with sodium nitrite and hydrochloric acid followed by copper (I) chloride) to form 4-chloro-2-fluoro-5-(4-methoxyphenoxy)nitrobenzene. Reduce the nitro group (e.g. by hydrogenating in ethanol with a catalytic amount of platinum oxide) to form the corresponding 4-chloro-2-fluoro-5-(4-methoxyphenoxy)aniline.

The compounds of the present invention wherein Z is S may be prepared using the following method:

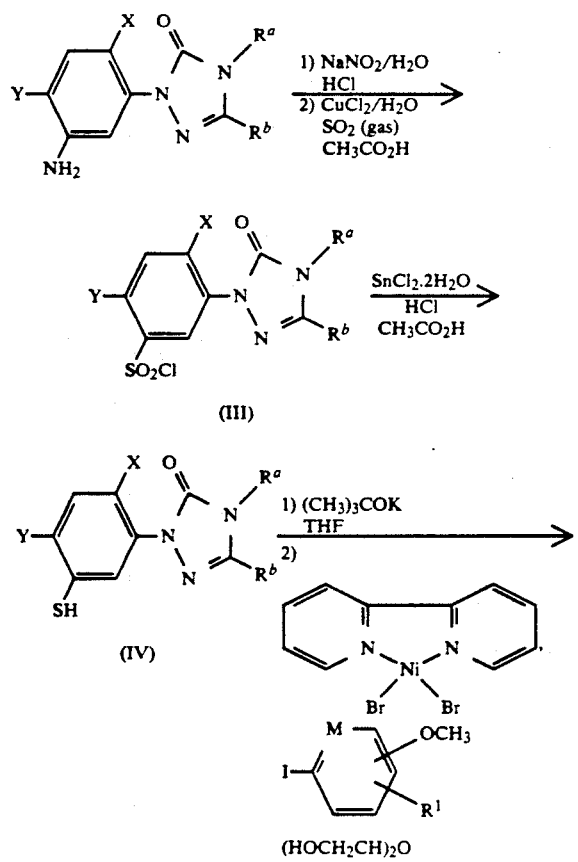

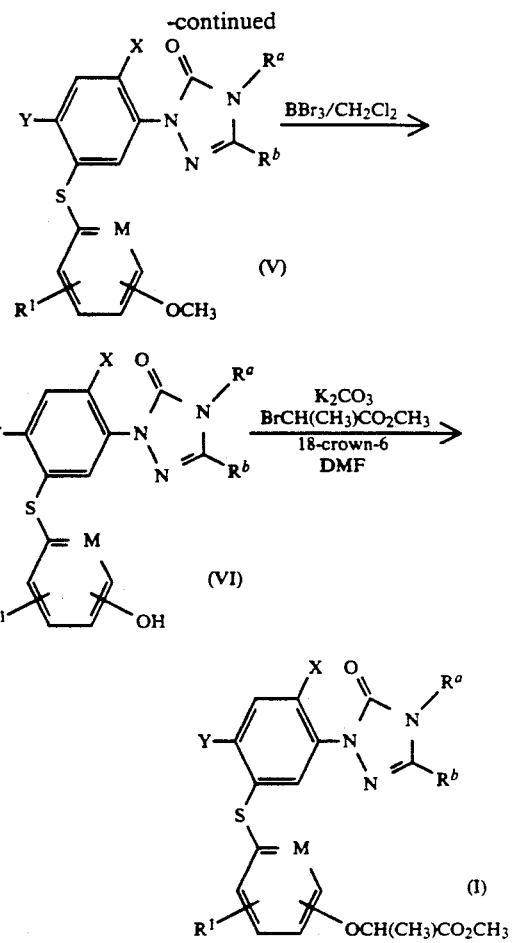

The reaction of an appropriately substituted 1-(5-aminophenyl)-4,5-dihydro-1,2,4-triazol-5(1H)-one with aqueous sodium nitrite and hydrochloric acid followed by the addition of aqueous copper II chloride, acetic acid and sulfur dioxide produced the correspondingly substituted 1-(5-chlorosulfonylphenyl)-4,5-dihydro-1,2,4-triazol-5(1H)-one (III). Treatment of (III) with stannous chloride dihydrate in acetic acid and hydrogen chloride gas yielded the substituted 1-(5-thiohydroxyphenyl)-4,5-dihydro-1,2,4-triazol-5(1H)-one (IV). The reaction of (IV) with potassium t-butoxide in tetrahydrofuran and then with an appropriately substituted iodoanisole or substituted iodomethoxypyridine in ethylene glycol in the presence of a small amount of bis(bipyridine)-nickel II bromide yielded the substituted 1-[5-(substituted-methoxyphenylthio)- or 1-[5-(substituted-methoxypyridinylthio)phenyl]-4,5-dihydro-1,2,4-triazol-5(1H)-one (V). Treatment of (V) with boron tribromide in methylene chloride produced the substituted 1-[5-(substituted-hydroxyphenylthio) or 1-[5-(substituted hydroxypyridinylthio)phenyl]-4,5-dihydro-1,2,4-triazol-5(1H)-one (VI). The reaction of (VI) with potassium carbonate, an appropriately substituted bromopropionate, and, if desired, a small amount of 1,4,7,10,13,16-hexaoxacyclooctadecane (18-crown-6) in N,N-dimethylformamide yielded a compound of formula I in which the Z group is S.

To prepare compounds of the present invention wherein Z is NH or alkyl amino the following method may be used:

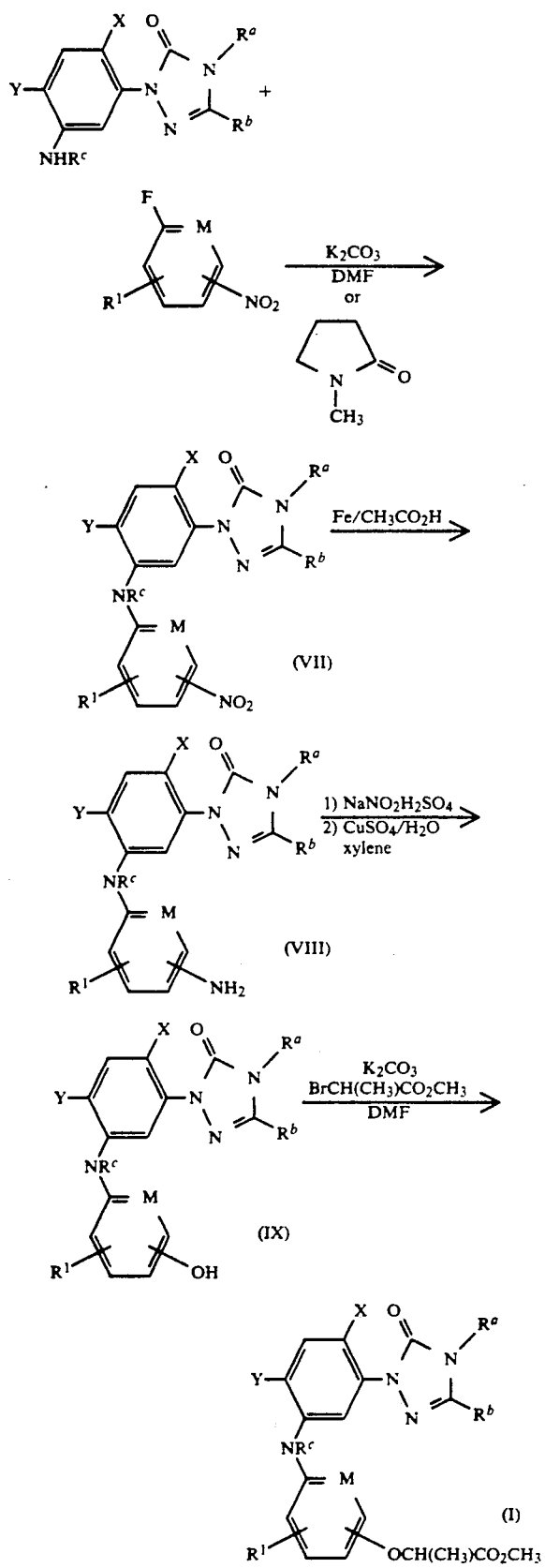

dine and potassium carbonate in a solvent such as N,N-dimethylformamide or 1-methyl-2-pyrrolidinone would produce the correspondingly substituted 1-[5-(substituted-nitrophenylamino)-or 1-[5-(substituted-nitropyridylamino)-4,5-dihydro-1,2,4-triazol-5(1H)-one (VII). The reduction of the nitro group of compound (VII) to an amino group, compound (VIII), would be accomplished by using iron filings and acetic acid. Subsequent treatment of (VIII) with sodium nitrite in sulfuric acid then with aqueous copper (II) sulfate in xylene would produce the substituted 1-[5-(substituted hydroxyphenylamino)- or 1-[5-(substituted hydroxypyridylamino)-4,5-dihydro-1,2,4-triazol-5(1H)-one (IX). The reaction of (IX) with potassium carbonate and an appropriately substituted bromopropionate in a solvent such as N,N-dimethylformamide would yield a compound of formula (I) in which the Z group is NH or an alkylamino.

It will be understood that substituents present in the final product may be introduced at various stages. For instance in methods D and E the methoxy group may be converted to a Q' group such as a $C_2H_5O—CO—CH(CH_3)—O—$ group at a subsequent stage in the process, or the latter group may be introduced earlier, as by using ethyl 2-bromopropionate in place of the methyl iodide in Method D or by using ethyl 2-(4-hydroxyphenoxy)-propionate in place of the 4-methoxyphenol in Method E.

EXAMPLE 1

ETHYL 2-[4-[(2-CHLORO-4-FLUORO-5-(4-DIFLUOROMETHYL-4,5-DIHYDRO-3-METHYL-5-OXO-1H-1,2,4-TRIAZOL-1-YL)PHENOXY]-PHENOXY]PROPIONATE

Step A

1-[4-Chloro-2-fluoro-5-(4-nitrophenoxy)phenyl]-4-difluoromethyl-4,5-dihydro-3-methyl-1,2,4-triazol-5(1H)-one To a stirred mixture of 0.91 g (0.019 mole) of sodium hydride in 30 mL of N,N-dimethylformamide was added slowly a solution of 5.50 g (0.019 mole) of 1-[4-chloro-2-fluoro-5-hydroxyphenyl)-4-difluoromethyl-4,5-dihydro-3-methyl-1,2,4-triazol-5(1H)-one in 30 mL of N,N-dimethylformamide. To this mixture was added 2.68 g (0.019 mole) of 4-fluoronitrobenzene. The resultant mixture was stirred at room temperature for approximately 18 hours and then was heated at 80° C. for one hour. The mixture was allowed to cool and was poured into ice water. The aqueous mixture was extracted with diethyl ether. The extract was dried over anhydrous magnesium sulfate and filtered. The filtrate was evaporated under reduced pressure to yield 6.0 g of 1-[4-chloro-2-fluoro-5-(4-nitrophenoxy)phenyl]-4-difluoromethyl-4,5-dihydro-3-methyl-1,2,4-triazol-5(1H)-one as a solid, m.p. 115°–117° C., Compound 4 of Table 1.

The nmr spectrum was consistent with the proposed structure.

Step B

1-[5-(4-Aminophenoxy)-4-chloro-2-fluorophenyl]-4-difluoromethyl-4,5-dihydro-3-methyl-1,2,4-triazol-5-(1H)-one Hydrogenation of 5.80 g (0.015 mole) of 1-[4-chloro-2-fluoro-5-(4-nitrophenoxy)phenyl]-4-difluoromethyl- The reaction of an appropriately substituted 1-(5-aminophenyl)-4,5-dihydro-1,2,4-triazol-5(1H)-one with an appropriately substituted fluoronitrobenzene or pyri- 4,5-dihydro-3-methyl-1,2,4-triazol-5(1H)-one dissolved in 100 mL of ethanol in the presence of a catalytic amount (0.30 g) of platinum oxide produced 4.6 g of 1-[5-(4-aminophenoxy)-4-chloro-2-fluorophenyl]-4-difluoromethyl-4,5-dihydro-3-methyl-1,2,4-triazol-5(1H)-one as a solid, m.p. 133°–135° C., Compound 3 of Table 1.

The nmr spectrum was consistent with the proposed structure.

Step C
1-[4-Chloro-2-fluoro-5-(4-hydroxyphenoxy)-phenyl]-4-difluoromethyl-4,5-dihydro -3-methyl-1,2,4-triazol-5(1H)-one While maintaining a temperature of 20° to 25° C., 4.4 g (0.011 mole) of 1-[5-(4-aminophenoxy)-4-chloro-2-fluorophenyl]-4-difluoromethyl-4,5-dihydro -3-methyl-1,2,4-triazol-5(1H)-one was added to 4.0 mL of stirred, concentrated sulfuric acid. To this was added a solution of 0.89 g (0.13 mole) of sodium nitrite dissolved in 6.0 mL of water, while continuing to maintain a temperature of about 20° C. After complete addition, the mixture was stirred at 20° C. for 30 minutes. This mixture was added through a glass tube to the bottom of a stirred, refluxing mixture of 32.0 g (0.13 mole) of copper (II) sulfate pentahydrate, 80 mL of water and 30 mL of xylene. After complete addition the mixture was refluxed for one hour. The mixture was cooled, and the organic phase was separated from the aqueous phase. The organic phase was extracted with an aqueous, sodium hydroxide solution (6.0 g of sodium hydroxide pellets dissolved in 250 mL of water). The basic extract was neutralized with concentrated hydrochloric acid, causing a precipitate to form. The solid was collected by filtration to yield 2.3 g of 1-[4-chloro-2-fluoro-5-(4-hydroxyphenoxy)phenyl]-4-difluoromethyl-4,5-dihydro-3-methyl-1,2,4-triazol-5-(1H)-one, m.p. 162°–162° C., Compound 2 of Table 1.

Step D Ethyl
2-[4-[(2-chloro-4-fluoro-5-(4-difluoromethyl-4,5-dihydro-3-methyl -5-oxo-1H-1,2,4-triazol-1-yl)phenoxy]phenoxy]propionate A stirred mixture of 0.60 g (0.0015 mole) of 1-[4-chloro-2-fluoro-5-(4-hydroxyphenoxy)phenyl]-4-difluoromethyl-4,5-dihydro-3-methyl-1,2,4-triazol-5(1H)-one, 0.54 g (0.0030 mole) of ethyl 2-bromopropionate, and 0.32 q (0.0023 mole) of potassium carbonate in 30 mL of acetone was heated at reflux for six days. The mixture was cooled and filtered. The filtrate was evaporated under reduced pressure leaving a residue. This residue was purified by column chromatography on silica gel, eluting with methylene chloride to yield 0.43 g of ethyl 1-[4-[(2-chloro-4-fluoro-5-(4-difluoromethyl-4,5-dihydro-3-methyl-5-oxo -1H-1,2,4-triazol-1-yl)phenoxy]-phenoxy]propionate as a solid, m.p. 128°–129° C., Compound 5 of Table 1.

The nmr spectrum was consistent with the proposed structure.

EXAMPLE 2
N-METHYLSULFONYL-2-[4-[2-CHLORO-4-FLUORO-5-(4-DIFLUOROMETHYL-4,5-DIHYDRO-3-METHYL -5-OXO-1H 1,2,4-TRIAZOL-1-YL)PHENOXY]PHENOXY]-PROPIONAMIDE

In a manner similar to Step D of Example 1, the reaction of 0.60 g (0.0015 mole) of 1-[4-chloro-2-fluoro-5-(4-hydroxyphenoxy)phenyl]-4-difluoromethyl-4,5-dihydro-3-methyl-1,2,4-triazol-5(1H)-one, 0.32 g (0.0014 mole) of N-methylsulfonyl-2-bromopropionamide, and 0.24 g (0.0017 mole) of potassium carbonate in 20 mL of acetone produced 0.3 g of N-methylsulfonyl-2-[4-[2-chloro-4-fluoro-5-(4-difluoromethyl-4,5 -dihydro-3-methyl-5-oxo-1H-1,2,4-triazol-1-yl)phenoxy]phenoxy]-propionamide as an oil, Compound 32 of Table 1.

The nmr spectrum was consistent with the proposed structure.

EXAMPLE 3
METHYL 2-[2-[2-CHLORO-4-FLUORO-5-(4-DIFLUOROMETHYL-4,5-DIHYDRO-3-METHYL-5-OXO -1H-1,2,4-TRIAZOL-1-YL)PHENOXY]PYRIDIN-5-YLOXY]PROPIONATE

Step A
1-[4-Chloro-2-fluoro-5-(5-nitropyridin-2-yloxy)phenyl]-4-difluoromethyl-4,5-dihydro-3-methyl-1,2,4-triazol-5(1H)-one To a stirred mixture of 5.0 g (0.017 mole) of 1-(4-chloro-2-fluoro-5-hydroxyphenyl)-4-difluoromethyl-4,5-dihydro-3-methyl-1,2,4-triazol-5(1H)-one and 2.6 g (0.019 mole) of potassium carbonate in 25 mL of acetone was added 2.7 g (0.017 mole) of 2-chloro-5-nitropyridine. The mixture was stirred at room temperature for one hour, then was heated at reflux for two hours. The mixture was allowed to cool to room temperature and was stirred for approximately 18 hours. The reaction mixture was heated at reflux for an additional four hours, then cooled and stirred at room temperature for approximately 18 hours. The mixture was filtered, and the filtrate was evaporated under reduced pressure to leave an oily residue, which crystallized upon standing to give 7.0 g of 1-[4-chloro-2-fluoro-5-(5-nitropyridin-2-yloxy)phenyl]-4-difluoromethyl -4,5-dihydro-3-methyl-1,2,4-triazol-5(1H)-one, m.p. 120°–123° C.

The nmr spectrum was consistent with the proposed structure.

Step B
1-[5-(5-Aminopyridin-2-yloxy)-4-chloro-2-fluorophenyl]-4-difluoromethyl-4,5-dihydro-3-methyl-1,2,4-triazol-5(1H)-one Iron filings (3.6 g, 0.064 mole) were added slowly to a stirred mixture of 7.0 g (0.017 mole) of 1-[4-chloro-2-fluoro-5-(5-nitropyridin-2-yloxy) phenyl]-4-difluoromethyl-4,5-dihydro-3-methyl-1,2,4-triazol-5(1H)-one, 25 mL of glacial acetic acid, 12 mL of tetrahydrofuran, and 5 mL of water. The reaction mixture was stirred at room temperature for three hours and was then diluted with 20 mL of diethyl ether. The mixture was filtered through a pad of Celite ® filter aid, and the filtrate was stored at 5° C. to 10° C. for approximately 18 hours. The filtrate was neutralized by the addition of solid sodium bicarbonate and water. The organic phase was separated from the aqueous phase. The aqueous phase was extracted several times with diethyl ether, and the extracts were combined with the organic phase. The combined organic phase was washed first with water, then with an aqueous, saturated sodium chloride solution. The organic phase was dried over anhydrous magnesium sulfate and filtered. The filtrate was evaporated under reduced pressure to yield 6.0 g of 1-[5-(5-aminopyridin-2-yloxy)-4-chloro-2-fluorophenyl]-4-difluoromethyl-4,5-dihydro-3-methyl-1,2,4-triazol-5(1H)-one as a solid.

Analysis of this compound by thin layer chromatography showed it to be the same as a previously prepared sample the melting point of which was 138°-140° C. and the nmr spectrum of which was consistent with the proposed structure.

Step C

2-[2-Chloro-4-fluoro-5-(4-difluoromethyl-4,5-dihydro-3-methyl-5-oxo-1H -1,2,4-triazol-1-yl)phenoxy]pyridine-5-diazonium tetrafluoroborate To a stirred mixture of 3.9 g (0.010 mole) of 1-[5-(5-aminopyridin-2-yloxy)-4-chloro-2-fluorophenyl]-4-difluoromethyl-4,5-dihydro-3-methyl-1,2,4-triazol-5(1H)-one in 10 mL of water was added 5.0 mL of concentrated hydrochloric acid. The mixture was cooled in an ice water bath, and a solution of 0.76 g (0.011 mole) of sodium nitrite in 1.4 mL of water was added portionwise. The resultant mixture was stirred at 0° C. for 30 minutes, and a solution of 1.5 g (0.014 mole) of sodium tetrafluoroborate in 5 mL of water was added portionwise. An additional 5 mL of water was added, and the reaction mixture was stirred at 0° C. for 45 minutes. The mixture was filtered, and the filter cake was rinsed with ice water followed by diethyl ether. The filter cake was dried under reduced pressure to yield 4.7 g of 2-[2-chloro-4-fluoro-5-(4-difluoromethyl-4,5-dihydro -3-methyl-5-oxo-1H-1,2,4-triazol-1-yl)phenoxy]pyridine-5-diazonium tetrafluoroborate.

Step D

1-[4-Chloro-2-fluoro-5-(5-hydroxypyridin-2-yloxy)-phenyl]-4-difluoromethyl-4,5 -dihydro-3-methyl-1,2,4-triazol-5(1H)-one To a stirred, cold (ice bath) solution of 0.67 g (0.0048 mole) of potassium carbonate in 20 mL of trifluoroacetic acid was added 4.7 g (0.097 mole) of 2-[2-chloro-4-fluoro-5-(4-difluoromethyl-4,5-dihydro -3-methyl-5-oxo-1H-1,2,4-triazol-1-yl)phenoxy]pyridine-5-diazonium tetrafluoroborate. The reaction mixture was allowed to warm to room temperature and was then heated at reflux for 5.5 hours. The mixture was cooled to room temperature, diluted with 50 mL of water, and the whole was extracted with four portions of methylene chloride. The extracts were combined, dried over anhydrous magnesium sulfate, and filtered. The filtrate was evaporated under reduced pressure to give a red oil which was purified by column chromatography on silica gel. Elution with n-hexane:ethyl acetate (2:1) gave 3.3 g of 1-[4-chloro-2-fluoro-5-(5-hydroxypyridin-2-yloxy)-phenyl]-4-difluoromethyl-4,5-dihydro -3-methyl,1,2,4-triazol-5(1H)-one as a solid, m.p. 179°-181° C.

Step E Methyl

2-[2-[2-chloro-4-fluoro-5-(4-difluoromethyl-4,5-dihydro-3-methyl-5 -oxo-1H-1,2,4-triazol-1-yl)phenoxy]pyridin-5-yloxy]-propionate Under a dry nitrogen atmosphere, 0.28 g (0.0017 mole) of methyl 2-bromopropionate was added to a stirred solution of 0.60 g (0.0016 mole) of 1-[4-chloro-2-fluoro-5-(5-hydroxypyridin-2-yloxy)phenyl ]-4-difluoromethyl-4,5-dihydro-3-methyl-1,2,4-triazol-5(1H)-one and 0.32 g (0.0023 mole) of potassium carbonate in 10 mL of acetone. The reaction mixture was stirred at room temperature for one hour, then was heated at reflux for approximately 18 hours. The mixture was cooled to room temperature and was filtered. The filtrate was evaporated under reduced pressure leaving a residue which was purified by column chromatography on silica gel. Elution with n-hexane:ethyl acetate (1:1) gave 0.78 g of methyl 2-[2-[2-chloro-4-fluoro-5-(4-difluoro-methyl-4,5-dihydro-3-methyl -5-oxo-1H-1,2,4-triazol-1-yl)phenoxy]pyridin-5-yloxy]propionate as a yellow oil.

The nmr and IR spectra were consistent with the proposed structure.

EXAMPLE 4

2-[2-[2-CHLORO-4-FLUORO-5-(4-DIFLUOROMETHYL-4,5-DIHYDRO-3-METHYL-5-OXO-1H -1,2,4-TRIAZOL-1-YL)PHENOXY]PYRIDIN-5-YLOXY]PROPIONIC ACID

A mixture of 1.2 g (0.0023 mole) of t-butyl 2-[2-[2-chloro-4-fluoro-5-(4-difluoromethyl -4,5-dihydro-3-methyl-5-oxo-1H-1,2,4-triazol-1-yl)phenoxy]pyridin-5-yloxy]propionate (prepared by the method of Example 3, Step E using t-butyl 2-chloropropionate) in 7 mL of trifluoroacetic acid was stirred at room temperature for 30 minutes. The excess trifluoroacetic acid was removed by evaporation under reduced pressure leaving an oil. The oil was partitioned between diethyl ether and water. The organic phase was separated, dried over anhydrous magnesium sulfate, and filtered. The filtrate was evaporated under reduced pressure leaving a thick oil. Upon standing, the oil crystallized as a white solid. The solid was triturated with petroleum ether to give 0.66 g of 2-[2-[2-chloro-4-fluoro-5-(4-difluoromethyl-4,5-dihydro-3-methyl-5-oxo-1H-1,2,4-triazol-1- yl)phenoxy]pyridin-5-yloxy]propionic acid, m.p. 49°-51° C.

The nmr and IR spectra were consistent with the proposed structure.

EXAMPLE 5

N-(1-METHYLETHYL)SULFONYL-4-[2-CHLORO-4-FLUORO-5-(4-DIFLUOROMETHYL-4,5 -DIHYDRO-3-METHYL-5-OXO-1H-1,2,4-TRIAZOL-1-YL)PHENOXY]PHENYLCARBOXAMIDE

Step A

1-[4-Chloro-5-(4-cyanophenoxy)-2-fluorophenyl]-4-difluoromethyl-4,5-dihydro -3-methyl-1,2,4-triazol-5(1H)-one To a stirred solution of 5.0 g (0.017 mole) of 1-(4-chloro-2-fluoro-5-hydroxyphenyl)-4-difluoromethyl-4,5-dihydro-3-methyl-1,2,4-triazol-5(1H)-one in 150 mL of N,N-dimethylformamide was added 2.8 g (0.020 mole) of potassium carbonate. The resultant mixture was stirred for ten minutes, and 2.1 g (0.017 mole) of 4-fluorobenzonitrile was added. The mixture was stirred and heated at 120° C. for approximately 18 hours. The solvent was removed from the mixture by distillation under reduced pressure leaving a residue which was partitioned between diethyl ether and water. The organic phase was separated, dried over anhydrous magnesium sulfate, and filtered. The filtrate was evaporated under reduced pressure to give 4.4 g of 1-[4-chloro-5-(4-cyanophenoxy)-2-fluorophenyl]-4-difluoromethyl -4,5-dihydro-3-methyl-1,2,4-triazol-5(1H)-one as a solid.

A previously prepared sample of this compound, prepared in the manner described above, had a melting point of 175°-177° C. and an nmr spectrum which was consistent with the proposed structure.

Step B Methyl 4-[2-chloro-4-fluoro-5-(4-difluoromethyl-4,5-dihydro-3-methyl-5-oxo -1H-1,2,4-triazol-1-yl)phenoxy]phenylcarboxylate A solution of 4.4 g (0.011 mole) of 1-[4-chloro-5-(4-cyanophenoxy)-2-fluorophenyl]-4-diffluoromethyl-4,5-dihydro-3-methyl-1,2,4-triazol-5(1H)-one in 200 mL of methanol was stirred at room temperature while gaseous hydrogen chloride was bubbled into the solution. After approximately 15 minutes, the hydrogen chloride flow was stopped, and the reaction mixture was heated at reflux for approximately 18 hours. Additional hydrogen chloride gas was bubbled into the reaction mixture two more times during a three day period, the mixture being cooled during addition and heated following addition. The reaction mixture was cooled, and the solvent was removed by evaporation under reduced pressure leaving a residue. The residue was partitioned between diethyl ether and water. The organic phase was separated, dried over anhydrous magnesium sulfate, and filtered. The filtrate was evaporated under reduced pressure leaving an oil. The oil was purified by column chromatography on silica gel, eluting with n-heptane:ethyl acetate (85:15) to give 1.8 g of methyl 4-[2-chloro-4-fluoro-5-(4-difluoromethyl-4,5-dihydro -3-methyl-5-oxo-1H-1,2,4-triazol-1-yl)phenoxy]phenylcarboxylate as a solid, m.p. 97°-98° C., Compound 126 of Table 1.

The nmr and IR spectra were consistent with the proposed structure.

Step C 4-[2-Chloro-4-fluoro-5-(4-difluoromethyl-4,5-dihydro-3-methyl-5-oxo-1H -1,2,4-triazol-1-yl)phenoxy]phenylcarboxylic acid To a stirred mixture of 1.8 g (0.0042 mole) of methyl 4-[2-chloro-4-fluoro-5-(4-difluoromethyl-4,5-dihydro-3-methyl-5-oxo-1H-1,2,4 -triazol-1-yl)phenoxy]-phenylcarboxylate and 1.3 g (0.0029 mole) of ethyl 4-[2-chloro-4-fluoro-5-(4-difluoromethyl-4,5-dihydro -3-methyl-5-oxo-1H-1,2,4-triazol-1-yl)phenoxy]phenylcarboxylate (prepared by the method of Step B using ethanol in place of methanol) in 20 mL of tetrahydrofuran was added a solution of 0.58 g (0.014) of sodium hydroxide in 30 mL of water. The reaction mixture was heated at 50° C. for 1.5 hour, then was stirred at room temperature for approximately 18 hours. The mixture was again heated at 50° C. for two hours and then was allowed to cool. The solvent was removed from the mixture by evaporation under reduced pressure leaving a residue. The residue was stirred in a 2N hydrochloric acid solution, and the resultant mixture was extracted successively with diethyl ether and ethyl acetate. The organic phases were combined, dried over anhydrous magnesium sulfate, filtered, and the filtrate concentrated under reduced pressure to give a solid residue. The residue was purified by column chromatography on silica gel, eluting with methylene chloride:methanol (95:5) to give 2.5 g of 4-[2-chloro-4-fluoro-5-(4-difluoromethyl-4,5-dihydro-3-methyl-5-oxo 1H-1,2,4-triazol-1-yl)phenoxy]phenylcarboxylic acid as a solid, m.p. 184°-185° C.

Step D 4-[2-Chloro-4-fluoro-5-(4-difluoromethyl-4,5-dihydro-3-methyl-5-oxo-1H -1,2,4-triazol-1-yl)phenoxy]phenylcarboxylic acid chloride.

A stirred solution of 1.7 g (0.0041 mole) of 4-[2-chloro-4-fluoro-5-(4-difluoromethyl-4,5-dihydro-3-methyl-5-oxo-1H-1,2,4-triazol-1-yl)phenoxy]phenylcarboxylic acid in 75 mL of thionyl chloride was heated at reflux for four hours. The excess thionyl chloride was removed by distillation under reduced pressure to yield 4-[2-chloro-4-fluoro-5-(4-difluoromethyl-4,5-dihydro-3-methyl-5-oxo-1H-1,2,4-triazol-1-yl)phenoxy]-phenylcarboxylic acid chloride as a yellow oil.

Step E N-(1-Methylethyl)sulfonyl-4-[2-chloro-4-fluoro-5-(4-difluoromethyl-4,5-dihydro -3-methyl-5-oxo-1H-1,2,4-triazol-1-yl)phenoxy]phenylcarboxamide A stirred mixture of 0.59 g (0.0014 mole) of 4-[2-chloro-4-fluoro-5-(4-difluoromethyl -4,5-dihydro-3-methyl-5-oxo-1H-1,2,4 triazol-1-yl)phenoxy]phenylcarboxylic acid chloride and 0.17 g (0.0014 mole) of 2-sulfamylpropane was heated at 195° C. for approximately 15 minutes. The mixture was cooled and 2 mL of methylene chloride was added. The mixture was allowed to stand at room temperature for approximately 18 hours. A brown solid formed, was collected and triturated with petroleum ether. Recovery of the solid by filtration gave 0.58 g of N-(1-methylethyl)sulfonyl-4-[2-chloro-4-fluoro-5-(4-difluoromethyl-4,5-dihydro-3-methyl-5-oxo-1H-1,2,4-triazol-1-yl)phenoxy]phenylcarboxamide as a solid, m.p. 185°-187° C., Compound 130 of Table 1.

The nmr and IR spectra were consistent with the proposed structure.

EXAMPLE 6

1-[2,4-DICHLORO-5-(4-NITROPHENOXY)-PHENYL]-4-DIFLUOROMETHYL-4,5-DIHYDRO-3-METHYL -1,2,4-TRIAZOL-5-(1H)-ONE

A stirred mixture of 1.0 g (0.0032 mole) of 1-(2,4-dichloro-5-hydroxyphenyl)-4-difluoromethyl -4,5-dihydro-3-methyl-1,2,4-triazol-5(1H)-one, 0.66 g (0.0048 mole) of potassium carbonate, and 0.76 g (0.0048 mole) of 4-chloronitrobenzene in 20 ml of N,N-dimethylformamide was heated at 120° C. for approximately 18 hours. The reaction mixture was cooled and was poured into ice-water. This aqueous mixture was neutralized with hydrochloric acid and then was extracted with ethyl acetate. The organic phase was washed with water and then was dried over anhydrous magnesium sulfate. This mixture was filtered, and the filtrate was evaporated under reduced pressure leaving an orange oil. The orange oil was purified by column chromatography on silica gel, eluting with methylene chloride to yield 1.2 g of 1-[2,4-dichloro-5-(4-nitrophenoxy)-phenyl]-4-difluoromethyl-4,5-dihydro-3-methyl-1,2,4-triazol-5(1H)-one as a solid, m.p. 99°-101° C., compound 92 of Table 1.

The nmr and ir spectra were consistent with the proposed structure.

EXAMPLE 7

METHYL 2-[4-[2,4-DICHLORO-5-(4-DIFLUOROMETHYL-4,5-DIHYDRO-3-METHYL-5-OXO-1H-1,2,4-TRIAZOL-1-YL)PHENOXY]-3-CHLOROPHENOXY]-PROPIONATE

Step A
1-[2,4-Dichloro-5-(2-chloro-4-nitrophenoxy)-phenyl]-4-difluoromethyl-4,5-dihydro-3-methyl-1,2,4-triazol-5-(1H)-one A mixture of 10.0 g (0.032 mole) of 1-(2,4-dichloro-5-hydroxyphenyl)-4-difluoromethyl-4,5-dihydro-3-methyl-1,2,4-triazol-5(1H)-one, 5.52 g (0.040 mole) of potassium carbonate, and 7.02 g (0.040 mole) of 3-chloro-4-fluoronitrobenzene in 60 ml of N,N-dimethylformamide was stirred at room temperature for approximately 18 hours. The reaction mixture was poured into ice-water. This aqueous mixture was extracted with diethyl ether. The extract ;as dried over anhydrous magnesium sulfate and was filtered. The filtrate was evaporated under reduced pressure leaving a residue. This residue was purified by column chromatography on silica gel to yield 10.4 g of 1-[2,4-dichloro-5-(2-chloro-4-nitrophenoxy)phenyl]-4-difluoromethyl -4,5-dihydro-3-methyl-1,2,4-triazol-5(1H)-one as a solid, m.p. 135°-135.5° C., compound 179 of Table 1.

The nmr spectrum was consistent with the proposed structure.

1-[5-(4-Amino-2-chlorophenoxy)-2,4-dichlorophenyl]-4-difluoromethyl-4,5-dihydro-3-methyl-1,2,4-triazol-5(1H)-one To a stirred mixture of 10.0 g (0.021 mole) of 1-[2,4-dichloro-5-(2-chloro-4-nitrophenoxy) phenyl]-4-difluoromethyl-4,5-dihydro-3-methyl-1,2,4-triazol-5(1H)-one in 100 ml of glacial acetic acid and 5 ml of water was added slowly 10.0 g (0.179 mole) of iron powder. The reaction mixture was heated at 50° C. and then was allowed to cool to room temperature at which it was stirred for 1.5 hours. The mixture was poured into ice-water, and the aqueous mixture was extracted with diethyl ether. The extract was evaporated under reduced pressure leaving a residue. This residue was purified by column chromatography to yield 8.5 g of 1-[5-(4-amino-2-chlorophenoxy)-2,4-dichlorophenyl]-4-difluoromethyl-4,5-dihydro-3-methyl-1,2,4-triazol-5(1H)-one as a solid, m.p. 161°-162° C., compound 180 of Table 1.

Step C
1-[2,4-Dichloro-5-(2-chloro-4-hydroxyphenoxy)-phenyl]-4-difluoromethyl-4,5-dihydro-3-methyl-1,2,4-triazol-5(1H)-one In a manner similar to Step C of Example 1, 8.10 g (0.0186 mole) of 1-[5-(4-amino-2-chlorophenoxy)-2,4-dichlorophenyl]-4-difluoromethyl-4,5-dihydro-3-methyl-1,2,4-triazol-5(1H)-one in 60 ml of concentrated sulfuric acid was reacted with a solution of 1.30 g (0.019 mole) of sodium nitrite in 10 ml of water. Subsequent reaction of this mixture with a refluxing solution of 150.0 g (0.60 mole) of copper (II) sulfate pentahydrate in 150 ml of water and 1.50 ml of xylene yielded 2.6 g of 1-[2,4-dichloro-5-(2-chloro-4-hydroxyphenoxy)-phenyl]-4-difluoromethyl-4,5-dihydro-3-methyl-1,2,4-triazol-5(1H)-one, compound 181 of Table 1.

Step D Methyl 2-[4-[2,4-dichloro-5-(4-difluoromethyl-4,5-dihydro-3-methyl-5-oxo-1H-1,2,4-triazol-1-yl)phenoxy]-3-chlorophenoxy]propionate In a manner similar to Step D of Example 1, the reaction of 1.3 g (0.0029 mole) of 1-[2,4-dichloro-5-(2-chloro-4-hydroxyphenoxy)phenyl]-4-difluoromethyl-4,5-dihydro-3-methyl-1,2,4-triazol-5(1H)-one with 0.73 g (0.0044 mole) of methyl 2-bromopropionate and 0.60 g (0.0044 mole) of potassium carbonate in 60 ml of methyl ethyl ketone yielded 0.78 g of methyl 2-[4-[2,4-dichloro-5-(4-difluoromethyl-4,5-dihydro -3-methyl-5-oxo-1H-1,2,4-triazol-1-yl)phenoxy]-3-chlorophenoxy]-propionate as an oil, compound 150 of Table 1.

EXAMPLE 8

METHYL 2-[4-[2,4-DICHLORO-5-(4-DIFLUOROMETHYL-4,5-DIHYDRO-3-METHYL-5-OXO-1H-1,2,4-TRIAZOL-1-YL)PHENYLTHIO]PHENOXY]PROPIONATE

Step A 1
(2,4-Dichloro-5-chlorosulfonylphenyl)-4-difluoromethyl-4,5-dihydro-3-methyl-1,2,4-triazol-5(1H)-one A stirred mixture of 12.0 g (0.0388 mole) of 1-(5-amino-2,4-dichlorophenyl)-4-difluoromethyl-4,5-dihydro-3-methyl-1,2,4-triazol-5(1H)-one in 50 mL of hydrochloric acid was cooled to 0° C. A solution of 2.79 g (0.0405 mole) of sodium nitrite in 20 mL of water was added while maintaining a reaction temperature of approximately 0° C. After complete addition, the reaction mixture was allowed to warm to room temperature and stir for 1.5 hours. This mixture was added slowly to a solution of 5.44 g (0.0405 mole) of copper (II) chloride in 15 mL of water and 50 mL of acetic acid which was saturated with sulfur dioxide. The resultant mixture was stirred at room temperature for one hour, forming a precipitate. The reaction mixture was poured into ice water and was stirred for a brief period of time. This mixture was filtered to collect approximately 16 grams of 1-(2,4-dichloro-5-chlorosulfonylphenyl)-4-difluoromethyl-4,5-dihydro-3-methyl -1,2,4-triazol-5(1H)-one as an off-white solid.

Step B
1-(2,4-Dichloro-5-thiohydroxyphenyl)-4-difluoromethyl-4,5-dihydro-3-methyl -1,2,4-triazol-5(1H)-one Under a dry nitrogen atmosphere, a mixture of 26.4 g (0.117 mole) of stannous chloride dihydrate in 100 mL of acetic acid was stirred while hydrogen chloride gas was bubbled into the mixture. During this process, the mixture became a colorless solution (approximately five minutes), and the addition of hydrogen chloride gas was stopped. This solution was heated at 85° C., and a hot solution of 15.0 g (0.0388 mole) of 1-(2,4-dichloro-5-chlorosulfonylphenyl)-4-difluoromethyl-4,5-dihydro-3-methyl-1,2,4-triazol-5(1H)-one in 60 mL of acetic acid was added. The resultant mixture was heated at 85° C.

for 30 minutes. The reaction mixture was allowed to cool and was poured into 150 mL of hydrochloric acid. An aqueous, saturated solution of sodium chloride (120 mL) was added, and the resultant mixture was extracted three times with ethyl acetate. The organic extracts were combined and washed in succession with three portions of water and an aqueous, saturated sodium chloride solution. The washed organic phase was dried over anhydrous magnesium sulfate and was filtered. The filtrate was evaporated under reduced pressure, leaving a yellow solid. This solid was purified by column chromatography on silica gel to yield 4.85 grams of 1-(2,4-dichloro-5-thiohydroxyphenyl)-4-difluoromethyl -4,5-dihydro-3-methyl-1,2,4-triazol-5(1H)-one as a solid. The nmr spectrum was consistent with the proposed structure.

Step C
1-[2,4-Dichloro-5-(4-methoxyphenylthio)phenyl]-4-difluoromethyl-4,5-dihydro-3-methyl -1,2,4-triazol-5(1H)-one A solution of 4.85 g (0.0147 mole) of 1-(2,4-dichloro-5-thiohydroxyphenyl)-4-difluoromethyl -4,5-dihydro-3-methyl 1,2,4-triazol-5(1H)-one and 1.67 g (0.0149 mole) of potassium t-butoxide in 30 mL of tetrahydrofuran was stirred at room temperature for ten minutes. The solvent was removed from the reaction mixture by evaporation under reduced pressure, leaving a brown solid residue. To this residue was added 50 mL of ethylene glycol, 0.05 g (1.3 x 10-4 mole) of bis-(bipyridine)-nickel (II) bromide (prepared by the method of Cristau, et al., Organometallics, 4, 657-661, 1985), and 5.27 g (0.0224 mole) of 4-iodoanisole. This mixture was stirred and heated at 120° C. for approximately 65 hours. The reaction mixture was allowed to cool and was diluted with diethyl ether. This mixture was washed with three portions of water. The organic phase was dried over anhydrous magnesium sulfate and was filtered. The filtrate was evaporated under reduced pressure, leaving a purple oil. This oil was purified by column chromatography on silica gel, eluting with methylene chloride:petroleum ether (1:2) to yield 2.0 g of 1-[2,4-dichloro-5-(4-methoxyphenylthio)phenyl]-4-difluoro-methyl-4,5-dihydro-3-methyl-1,2,4-triazol-5(1H)-one as a solid, m.p. 134°-137° C. The nmr spectrum was consistent with the proposed structure.

Step D
1-[2,4-Dichloro-5-(4-hydroxyphenylthio)phenyl]-4-difluoromethyl-4,5-dihydro-3-methyl-1,2,4-triazol-5(1H)-one A solution of 2.5 g (0.0058 mole) of 1-[2,4-dichloro-5-(4-methoxyphenylthio)phenyl]-4-difluoromethyl-4,5-dihydro-3-methyl-1,2,4-triazol-5(1H)-one in 30 mL of methylene chloride was added slowly to 11.6 mL of a cold (−20° C.), stirred solution of one molar boron tribromide in methylene chloride. After complete addition, the reaction mixture was allowed to warm to room temperature and stir for approximately 18 hours. The reaction mixture was poured into ice-water forming a precipitate. This white solid was isolated by filtration; m.p. 230°-231° C. An nmr spectrum indicated that this was the desired product, 1-[2,4-dichloro-5-(4-hydroxyphenylthio)phenyl]-4-difluoromethyl -4,5-dihydro-3-methyl-1,2,4-triazol-5(1H)-one. The filtrate was washed with water, and the organic phase was evaporated under reduced pressure, leaving a brown solid. This brown solid was washed in succession with methylene chloride, diethyl ether, and ethyl acetate, leaving a white solid. Analysis of this solid by nmr spectroscopy indicated that it was product, m.p. 228°-229° C. The organic filtrates from washing the brown solid were combined and analyzed by thin layer chromatography. This analysis indicated product was present, and that product was removed by column chromatography on silica gel, eluting with diethyl ether:petroleum ether (1:1). A solid fraction obtained from this process was identified as product by nmr spectroscopy.

All solids which were identified as product were combined to yield 2.1 grams of 1-[2,4-dichloro-5-(4-hydroxyphenylthio)phenyl]-4-difluoromethyl -4,5-dihydro-3-methyl-1,2,4-triazol-5(1H)-one.

Step E
Methyl 2-[4-[2,4-dichloro-5-(4-difluoro-methyl-4,5-dihydro-3-methyl-5-oxo -1H-1,2,4-triazol-1-yl)phenylthio]phenoxy]-propionate A stirred mixture of 1.5 g (0.0036 mole) of 1-[2,4-dichloro-5-(4-hydroxyphenylthio)phenyl]-4-difluoromethyl-4,5-dihydro-3-methyl-1,2,4-triazol-5(1H)-one, 0.75 g (0.0054 mole) of potassium carbonate, 0.90 g (0.0054 mole) of methyl DL-2-bromopropionate, and 0.20 g ($8 \times 10^{-4}$ mole) of 18-crown-6 in 30 mL of N,N-dimethylformamide was heated at 100°-120° C. for approximately 18 hours. The reaction mixture was allowed to cool and was poured into ice-water. This aqueous mixture was extracted with diethyl ether and ethyl acetate. The organic extracts were combined and washed with water. The organic phase was dried over anhydrous magnesium sulfate and was filtered. The filtrate was evaporated under reduced pressure, leaving a yellow oil. This oil was purified by column chromatography on silica gel, eluting with diethyl ether:petroleum ether (40:60) to yield 0.83 g of methyl 2-[4-[2,4-dichloro-5-(4-difluoromethyl-4,5-dihydro-3-methyl-5-oxo-1H-1,2,4-triazol-1-yl)phenylthio]phenoxy]propionate as a solid, m.p. 100°-101° C. The nmr spectrum was consistent with the proposed compound.

EXAMPLE 9
1-[5-(4-AMINOPHENYL)AMINO-2,4-DICHLOROPHENYL]-4-DIFLUOROMETHYL-4,5-DIHYDRO-3-METHYL -1,2,4-TRIAZOL-5(1H)-ONE

Step A
1-[2,4-Dichloro-5-(4-nitrophenyl)aminophenyl]-4-difluoromethyl-4,5-dihydro-3-methyl-1,2,4-triazol-5(1H)-one To a stirred, cold (0° C.) mixture of 0.085 gram (0.00355 mole) of sodium hydride in 10 mL of N,N-dimethylformamide was added 1.0 gram (0.00323 mole) of 1-(5-amino-2,4-dichlorophenyl)-4-difluoromethyl-4,5-dihydro-3-methyl-1,2,4-triazol-5(1H)-one. After stirring for a brief period of time, 0.455 gram (0.00323 mole) of 4-fluoronitrobenzene was added. The resultant mixture was allowed to warm to room temperature and was stirred for one hour. The reaction mixture was heated at 60° C. for three hours and an additional 0.455 gram of 4-fluoronitrobenzene was added. This mixture was heated at 50° C. for approximately 18 hours. After cooling to room temperature, the mixture was poured into ice water. The aqueous mixture was extracted with three portions of ethyl acetate. The extracts were combined and washed in succession with 1N hydrochloric acid, an aqueous saturated sodium bicarbonate solution, water, and an aqueous sodium chloride solution. The washed organic phase was dried over anhydrous magnesium sulfate and was filtered. The filtrate was evaporated under reduced pressure to yield a solid. This solid was purified by recrystallization from ethyl acetate and n-heptane to yield 0.25 gram of 1-[2,4-dichloro-5-(4-nitrophenyl)-aminophenyl]-4-difluoromethyl-4,5-dihydro -3-methyl-1,2,4-triazol-5(1H)-one, m.p. 249°–251° C. The mother liquor from the recrystallization process was evaporated under reduced presure leaving 1.0 gram of an orange oil. Analysis of this oil by thin layer chromatography indicated it contained a substantial amount of the desired product.

Step B

1-[5-(4-Aminophenyl)amino-2,4-dichlorophenyl]-4-difluoromethyl-4,5-dihydro-3-methyl-1,2,4-triazol-5(1H)-one The hydrogenation of 1.0 gram of the orange oil from Step A with approximately 0.01 gram of platinum oxide in 50 mL of ethyl acetate produced an oil. This oil was purified by chromatography or a 4 mm Chromatatron ® chromatography plate to yield 0.17 gram of 1-[5-(4-aminophenyl)amino-2,4-dichlorophenyl]-4-difluoromethyl-4,5-dihydro-3-methyl-1,2,4-triazol-5(1H)-one as a solid, m.p. 196°–197° C. The nmr spectrum was consistent with the proposed structure.

Other compounds of the invention may be prepared by the methods exemplified above or by methods within the skill of the art.

HERBICIDAL ACTIVITY

The plant test species used in demonstrating the herbicidal activity of compounds of this invention include cotton (*Gossypium hirsutum* var. Stoneville), soybean (*Glycine max* var. Williams), field corn (*Zea mays* var. Agway 595S), wheat (*Triticum aestivium* var. Prodax), rice (*Oryza sativa* var. Labelle), morningglory (*Ipomea lacunosa* or *Ipomea hederacea*), velvetleaf (*Abutilon theophrasti*), barnyardgrass (*Echinochloa crus galli*), green foxtail (*Setaria viridis*), johnsongrass (*Sorghum halepense*), and wild mustard (*Brassica raber*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered, then drenched with the appropriate amount of a solution of the test compound in a mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiples thereof. The flats were placed in a green-house and watered regularly at the soil surface for 21 days at which time phytotoxicity data were recorded.

The flats for the postemergence test were placed in a greenhouse and watered for 8–10 days, then the foliage of the emerged test plants was sprayed with a solution of the test compound in acetone-water containing up to 0.5% sorbitan monolaurate. After spraying the foliage was kept dry for 24 hours, then watered regularly for 21 days, and phytotoxicity data recorded.

Herbicidal data at selected application rates are given for various compounds of the invention in Tables 3, 3A, 3B, 3C, 4 and 4A, 4B, 4C below. The test compounds are identified therein by numbers which correspond to those in Tables: 1, 1A, 1B, and 1C.

In Tables 3, 3A, 3B, 3C, 4, 4A, 4B, and 4C below:
"kg/ha" is kilograms per hectare, and
"% C" is percent control.

For herbicidal application, the compound is formulated into herbicidal compositions, by admixture, in herbicidally effective amounts, with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

For preemergence application these herbicidal compositions are usually applied either as sprays, dusts, or granules in the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank-mix for postemergence application to facilitate dispersion on the foliage and absorption by the plant.

Other useful formulations for herbicidal applications are emulsifiable concentrates. Emulsifiable concentrates are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing, or emulsifying agents used in agricultural formulations include, for example, the alkyl and alkylaryl sulfonates and sulfates and their sodium salts, polyhydric alcohols, and other types of surface active agents, many of which are available in commerce. The surface active agent, when used, normally comprises 1% to 15% by weight of the herbicidal composition.

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon® fluorinated hydrocarbons, may also be used. Water-soluble or water-dispersible granules are also useful formulations for herbicidal application of the present compounds. Such granular formations are free-flowing, non-dusty, and readily water-soluble or water-miscible. The soluble or dispersible granular formulations described in U.S. Pat. No. 3,920,442 are useful herein with the present herbicidal compounds.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, for example, 2 g/ha or lower, e.g. about 1 to 250 g/ha preferably about 4 to 30 g/ha.

Compounds of this invention in which $R^2$ is $R^3[CO-CH(R^4)-O]_n-$ or $NCCH(R^4)O-[CO-CH(R^4)-O]_m-$ are particularly suitable for "total vegetation control", i.e. control of emerged weeds in situations where residual herbicidal soil activity is undesirable. Thus, these compounds are highly effective when applied at low dosages to existing weed foliage, the dosages being such that the herbicide has little or no residual soil activity. This makes it possible for the farmer to plant seeds (or seedlings) safely within a short time (such as 3 to 7 days) before or after the application of the herbicide. Consequently, these herbicides are very suitable for clearing fields of weeds in the well known "no till" (or "reduced till", or "conservation till") farming methods, in which the soil is not tilled, or is tilled only in spaced, very narrow, seed-receiving rows (such as rows about an inch wide) before the crop seeds are planted. The absence of substantial residual herbicidal soil activity also makes these compounds very suitable for clearing weeds between existing crop plants, e.g. on plantations such as rubber, oil palm, banana or cocoa plantations, or on vineyards or orchards, such as in the interspaces and around the bases of trees and vines. The herbicides are also suitable for use as foliar-applied, pre-harvest crop desiccants, e.g. for treating mature cotton, potato, soybean or sunflower plants. For many of these uses the present commercially available herbicides are paraquat and glyphosate. The herbicides of this invention are superior to those materials in that they are effective at much lower rates of application, are less toxic, and are more effective on broadleaf weeds.

For "total vegetation control", as described above, the compounds of the invention may be applied in an effective amount and concentration; the amount may be as low as about 1 to 250 g/ha, preferably about 30 to 250 g/ha. For example, in no-till or reduced till farming, the following approximate rates of application may be used for the following compounds:
compound no. 5: 30 to 125 g/ha;
compound no. 7: 30 to 125 g/ha;
compound no. 149: 63 to 250 g/ha;
compound no. 113: 63 to 250 g/ha; and
compound no. 54: 30 to 125 g/ha.

The compounds in which $R^2$ is $R^3[CO-CH(R^4)-O]_n-$ or $NCCH(R^4)O-]CO-CH(R^4)-O]_m-$ may be supplied in various types of formulations. The compounds may be sold to the user as emulsifiable concentrates which the user dilutes with water before spraying. As described earlier in this application, the emulsifiable concentrates are liquid compositions dispersible in water and may contain a liquid carrier (such as heavy aromatic naphtha) or may contain suspended solid herbicidal compound without such a carrier; in the latter case the concentrates are usually termed "flowable concentrates". Some of the foregoing compounds (such as compounds nos. 5, 7 and 82) are solids which are only slightly soluble (e.g. solubility less than 5%, such as less than 3%) in the usual aromatic solvents used as carriers in emulsifiable concentrates. It is therefore preferred to formulate the slightly soluble herbicidal compounds in the form of flowable concentrates containing very fine suspended particles (e.g. particles of average particle size less than 10 microns, such as 3 to 5 microns or less). Typical flowable concentrates may have formulations along the following lines:

| Component: | | % by Wt. |
|---|---|---|
| Active ingredient | | 46.00 |
| Colloidal magnesium aluminum silicate | | 0.40 |
| Sodium alkylnaphthalenesulfonate | | 2.00 |
| Paraformaldehyde | | 0.10 |
| Water | | 40.70 |
| Propylene glycol | | 7.50 |
| Acetylenic alcohols | | 2.50 |
| Xanthan gum | | 0.80 |
| | Total | 100.00 |
| Active ingredient | | 45.00 |
| Water | | 48.50 |
| Purified smectite clay | | 2.00 |
| Xanthan gum | | 0.50 |
| Sodium alkylnaphthalenesulfonate | | 1.00 |
| Acetylenic alcohols | | 3.00 |
| | Total | 100.00 |

The relatively insoluble compounds may also be supplied as solutions in such polar water-miscible solvents as N-methyl pyrrolidone; such solutions are then diluted with water and used for spraying without delay.

The more soluble compounds (such as compounds 54, 149 and 174) may be supplied as emulsifiable concentrates, as well as in the form of flowable concentrates. Typical emulsifiable concentrates may have formulations along the following lines:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

It has been found that the herbicidal action of the compounds which are sparingly soluble in aromatic hydrocarbons, as well as those which are readily soluble in such hydrocarbons, is considerably increased (especially as to control of grasses) when the composition being sprayed on the foliage contains a substantially non-volatile aliphatic oil (e.g. of the type known as a "crop oil concentrate" or "oil concentrate") as an adjuvant. Such an adjuvant may be a hydrocarbon oil or a vegetable oil. The oil may be added with the water used to dilute the concentrate for spraying. The amount of such oil may be for example, about ⅔ quart to 1 ½ quarts per acre to be treated.

The active herbicidal compounds of this invention may be used in combination with other herbicides, e.g. they may be mixed with, say, an equal or larger amount of a known herbicide such as chloroacetanilide herbicide such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metolachlor), and N-chloroacetyl-N-(2,6-diethylphenyl)-glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl)benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

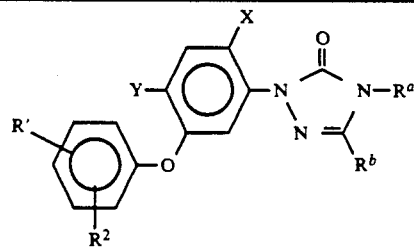

| Cmpd No. | $R^a$ | $R^b$ | $R^2$ | R' | X | Y |
|---|---|---|---|---|---|---|
| 1 | $CHF_2$ | $CH_3$ | 4-$NO_2$ | 3-CN | F | Cl |
| 2 | $CHF_2$ | $CH_3$ | 4-OH | H | F | Cl |
| 3 | $CHF_2$ | $CH_3$ | 4-$NH_2$ | H | F | Cl |
| 4 | $CHF_2$ | $CH_3$ | 4-$NO_2$ | H | F | Cl |
| 5 | $CHF_2$ | $CH_3$ | 4-OCH($CH_3$)$CO_2C_2H_5$ | H | F | Cl |
| 6 | $CHF_2$ | $CH_3$ | 4-OCH$_2$C≡CH | H | F | Cl |
| 7 | $CHF_2$ | $CH_3$ | 4-OCH($CH_3$)$CO_2CH_3$ | H | F | Cl |
| 8 | $CH_3$ | $CH_3$ | 4-OCH($CH_3$)$CO_2CH_3$ | H | F | Cl |
| 9 | CH($CH_3$)$_2$ | $CH_3$ | 4-OCH($CH_3$)$CO_2CH_3$ | H | F | Cl |
| 10 | $C_2H_5$ | $CH_3$ | 4-OCH($CH_3$)$CO_2CH_3$ | H | F | Cl |
| 11 | $CH_2CH_2CH_2F$ | $CH_3$ | 4-OCH($CH_3$)$CO_2CH_3$ | H | F | Cl |
| 12 | $CH_2CH_2F$ | $CH_3$ | 4-OCH($CH_3$)$CO_2CH_3$ | H | F | Cl |
| 13 | $CH_2CH_2CH_3$ | $CH_3$ | 4-OCH($CH_3$)$CO_2CH_3$ | H | F | Cl |
| 14 | $CH_2CH=CH_2$ | $CH_3$ | 4-OCH($CH_3$)$CO_2CH_3$ | H | F | Cl |
| 15 | $CH_2C≡CH$ | $CH_3$ | 4-OCH($CH_3$)$CO_2CH_3$ | H | F | Cl |
| 16 | $CHF_2$ | Cl | 4-OCH($CH_3$)$CO_2CH_3$ | H | F | Cl |
| 17 | $CHF_2$ | Br | 4-OCH($CH_3$)$CO_2CH_3$ | H | F | Cl |
| 18 | $CHF_2$ | F | 4-OCH($CH_3$)$CO_2CH_3$ | H | F | Cl |
| 19 | $CHF_2$ | CH($CH_3$)$_2$ | 4-OCH($CH_3$)$CO_2CH_3$ | H | F | Cl |
| 20 | $CHF_2$ | $SCH_3$ | 4-OCH($CH_3$)$CO_2CH_3$ | H | F | Cl |
| 21 | $CHF_2$ | $SO_2CH_3$ | 4-OCH($CH_3$)$CO_2CH_3$ | H | F | Cl |
| 22 | $CHF_2$ | $SCF_3$ | 4-OCH($CH_3$)$CO_2CH_3$ | H | F | Cl |
| 23 | $CHF_2$ | $SO_2CF_3$ | 4-OCH($CH_3$)$CO_2CH_3$ | H | F | Cl |
| 24 | $CHF_2$ | $C_2H_5$ | 4-OCH($CH_3$)$CO_2CH_3$ | H | F | Cl |
| 25 | $CHF_2$ | H | 4-OCH($CH_3$)$CO_2CH_3$ | H | F | Cl |
| 26 | $CHF_2$ | $CH_3$ | 4-OCH($CH_3$)$CO_2H$ | H | F | Cl |
| 27 | $CHF_2$ | $CH_3$ | 4-OCH($CH_3$)$CONH_2$ | H | F | Cl |
| 28 | $CHF_2$ | $CH_3$ | 4-OCH($CH_3$)$CONHCH_3$ | H | F | Cl |
| 29 | $CHF_2$ | $CH_3$ | 4-OCH($CH_3$)$CON(CH_3)_2$ | H | F | Cl |
| 30 | $CHF_2$ | $CH_3$ | 4-OCH($CH_3$)$CON(CH_3)OCH_3$ | H | F | Cl |
| 31 | $CHF_2$ | $CH_3$ | 4-OCH($CH_3$)$CON(CH_2CH=CH_2)_2$ | H | F | Cl |
| 32 | $CHF_2$ | $CH_3$ | 4-OCH($CH_3$)$CONHSO_2CH_3$ | H | F | Cl |
| 33 | $CHF_2$ | $CH_3$ | 4-OCH($CH_3$)$CON(CH_3)SO_2CH_3$ | H | F | Cl |
| 34 | $CHF_2$ | $CH_3$ | 4-OCH($CH_3$)$CON(C_2H_5)SO_2CH_3$ | H | F | Cl |
| 35 | $CHF_2$ | $CH_3$ | 4-OCH($CH_3$)$CONHSO_2CF_3$ | H | F | Cl |

TABLE 1-continued

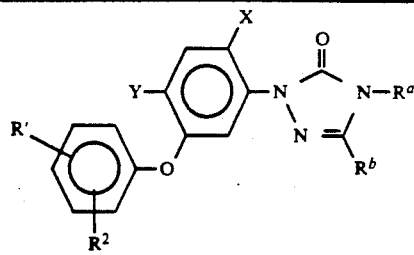

| Cmpd No. | $R^a$ | $R^b$ | $R^2$ | R' | X | Y |
|---|---|---|---|---|---|---|
| 36 | $CHF_3$ | $CH_3$ | 4-OCH($CH_3$)CON($CH_3$)$SO_2CF_3$ | H | F | Cl |
| 37 | $CHF_2$ | $CH_3$ | 4-OCH($CH_3$)CONHSO$_2$C$_2$H$_5$ | H | F | Cl |
| 38 | $CHF_2$ | $CH_3$ | 4-OCH($CH_3$)CONHSO$_2$C$_3$H$_7$ | H | F | Cl |
| 39 | $CHF_2$ | $CH_3$ | 4-OCH($CH_3$)CONHSO$_2$C$_6$H$_5$ | H | F | Cl |
| 40 | $CHF_2$ | $CH_3$ | 4-OCH($CH_3$)CONHSO$_2$(4-ClC$_6$H$_4$) | H | F | Cl |
| 41 | $CHF_2$ | $CH_3$ | 4-OCH($CH_3$)CONHSO$_2$(4-CH$_3$OC$_6$H$_4$) | H | F | Cl |
| 42 | $CHF_2$ | $CH_3$ | 4-OCH$_2$CONHSO$_2$CH$_3$ | H | F | Cl |
| 43 | $CHF_2$ | $CH_3$ | 4-OCH$_2$CO$_2$H | H | F | Cl |
| 44 | $CHF_2$ | $CH_3$ | 4-OCH$_2$CO$_2$C$_2$H$_5$ | H | F | Cl |
| 45 | $CHF_2$ | $CH_3$ | 4-OCH$_2$C≡N | H | F | Cl |
| 46 | $CHF_2$ | $CH_3$ | 4-OCH(CH$_3$)CN | H | F | Cl |
| 47 | $CHF_2$ | $CH_3$ | 4-OCH(CH$_3$)CO$_2$CH(CH$_3$)C≡CH | H | F | Cl |
| 48 | $CHF_2$ | $CH_3$ | 4-OCH$_2$COCH$_3$ | H | F | Cl |
| 49 | $CHF_2$ | $CH_3$ | 3-OCH(CH$_3$)CO$_2$C$_2$H$_5$ | H | F | Cl |
| 50 | $CHF_2$ | $CH_3$ | 3-OCH(CH$_3$)CO$_2$H | H | F | Cl |
| 51 | $CHF_2$ | $CH_3$ | 3-OCH(CH$_3$)CONH$_2$ | H | F | Cl |
| 52 | $CHF_2$ | $CH_3$ | 3-OCH(CH$_3$)CONHSO$_2$CH$_3$ | H | F | Cl |
| 53 | $CHF_2$ | $CH_3$ | 3-OCH(CH$_3$)CONHSO$_2$C$_6$H$_5$ | H | F | Cl |
| 54 | $CHF_2$ | $CH_3$ | 4-OCH(CH$_3$)CO$_2$C$_2$H$_5$ | 2-Cl | F | Cl |
| 55 | $CHF_2$ | $CH_3$ | 4-OCH(CH$_3$)CO$_2$C$_2$H$_5$ | 2-F | F | Cl |
| 56 | $CHF_2$ | $CH_3$ | 4-OCH(CH$_3$)CO$_2$C$_2$H$_5$ | 3-Cl | F | Cl |
| 57 | $CHF_2$ | $CH_3$ | 4-OCH(CH$_3$)CO$_2$C$_2$H$_5$ | 3-F | F | Cl |
| 58 | $CHF_2$ | $CH_3$ | 4-OCH(CH$_3$)CO$_2$C$_2$H$_5$ | 2-CH$_3$ | F | Cl |
| 59 | $CHF_2$ | $CH_3$ | 4-OCH(CH$_3$)CO$_2$C$_2$H$_5$ | 3-CH$_3$ | F | Cl |
| 60 | $CHF_2$ | $CH_3$ | 4-OCH(CH$_3$)CO$_2$C$_2$H$_5$ | 2-OCH$_3$ | F | Cl |
| 61 | $CHF_2$ | $CH_3$ | 4-OCH(CH$_3$)CO$_2$C$_2$H$_5$ | 3-OCH$_3$ | F | Cl |
| 62 | $CHF_2$ | $CH_3$ | 4-OCH(CH$_3$)CO$_2$C$_2$H$_5$ | 2-NO$_2$ | F | Cl |
| 63 | $CHF_2$ | $CH_3$ | 4-OCH(CH$_3$)CO$_2$C$_2$H$_5$ | 3-NO$_2$ | F | Cl |
| 64 | $CHF_2$ | $CH_3$ | 4-OCH(CH$_3$)CO$_2$C$_2$H$_5$ | 2,6-F$_2$ | F | Cl |
| 65 | $CHF_2$ | $CH_3$ | 4-OCH(CH$_3$)CO$_2$C$_2$H$_5$ | 2,3-F$_2$ | F | Cl |
| 66 | $CHF_2$ | $CH_3$ | 3-OCH(CH$_3$)CO$_2$C$_2$H$_5$ | 4-NO$_2$ | F | Cl |
| 67 | $CHF_2$ | $CH_3$ | 3-OCH(CH$_3$)CO$_2$C$_2$H$_5$ | 4-Cl | F | Cl |
| 68 | $CHF_2$ | $CH_3$ | 3-OCH(CH$_3$)CO$_2$C$_2$H$_5$ | 4-Br | F | Cl |
| 69 | $CHF_2$ | $CH_3$ | 3-OCH(CH$_3$)CO$_2$C$_2$H$_5$ | 4-F | F | Cl |
| 70 | $CHF_2$ | $CH_3$ | 3-OCH(CH$_3$)CO$_2$C$_2$H$_5$ | 6-F | F | Cl |
| 71 | $CHF_2$ | $CH_3$ | 3-OCH(CH$_3$)CO$_2$C$_2$H$_5$ | 4-CN | F | Cl |
| 72 | $CHF_2$ | $CH_3$ | 3-OCH(CH$_3$)CO$_2$C$_2$H$_5$ | 4-OCH$_3$ | F | Cl |
| 73 | $CHF_2$ | $CH_3$ | 4-OCH(CH$_3$)CO$_2$C$_2$H$_5$ | H | H | Br |
| 74 | $CHF_2$ | $CH_3$ | 4-OCH(CH$_3$)CO$_2$C$_2$H$_5$ | H | F | Br |
| 75 | $CHF_2$ | $CH_3$ | 4-OCH(CH$_3$)CO$_2$C$_2$H$_5$ | H | F | CH$_3$ |
| 76 | $CHF_2$ | $CH_3$ | 4-OCH(CH$_3$)CO$_2$C$_2$H$_5$ | H | F | NO$_2$ |
| 77 | $CHF_2$ | $CH_3$ | 4-OCH(CH$_3$)CO$_2$C$_2$H$_5$ | H | F | OCHF$_2$ |
| 78 | $CHF_2$ | $CH_3$ | 4-OCH(CH$_3$)CO$_2$C$_2$H$_5$ | H | F | CF$_3$ |
| 79 | $CHF_2$ | $CH_3$ | 4-OCH(CH$_3$)CO$_2$C$_2$H$_5$ | H | F | F |
| 80 | $CHF_2$ | $CH_3$ | 4-OCH(CH$_3$)CO$_2$C$_2$H$_5$ | H | F | SCH$_3$ |
| 81 | $CHF_2$ | $CH_3$ | 4-OCH(CH$_3$)CO$_2$C$_2$H$_5$ | H | H | Cl |
| 82 | $CHF_2$ | $CH_3$ | 4-OCH(CH$_3$)CO$_2$C$_2$H$_5$ | H | Cl | Cl |
| 83 | $CHF_2$ | $CH_3$ | 4-OCH(CH$_3$)CO$_2$C$_2$H$_5$ | H | Br | Cl |
| 84 | $CHF_2$ | $CH_3$ | 4-OCH(CH$_3$)CO$_2$C$_2$H$_5$ | H | CH$_3$ | Cl |
| 85 | $CHF_2$ | $CH_3$ | 4-OCH(CH$_3$)CO$_2$C$_2$H$_5$ | H | F | H |
| 86 | $CHF_2$ | $CH_3$ | 3-OCH(CH$_3$)CO$_2$C$_2$H$_5$ | 2,4-Cl$_2$ | H | H |
| 87 | $CHF_2$ | $CH_3$ | 3-OCH(CH$_3$)CO$_2$C$_2$H$_5$ | 2F,4Cl | H | H |
| 88 | $CHF_2$ | $CH_3$ | 4-OCH(CH$_3$)CO$_2$Na | H | F | Cl |
| 89 | $CHF_2$ | $CH_3$ | 4-OCH(CH$_3$)CO$_2$K | H | F | Cl |
| 90 | $CHF_2$ | $CH_3$ | 4-OCH(CH$_3$)CO$_2^-$N$^+$(C$_2$H$_5$)$_4$ | H | F | Cl |
| 91 | $CHF_2$ | $CH_3$ | 4-OCH(CH$_3$)CO$_2$CH(CH$_3$)$_2$ | H | F | Cl |
| 92 | $CHF_2$ | $CH_3$ | 4-NO$_2$ | H | Cl | Cl |
| 93 | $CHF_2$ | $CH_3$ | 4-NH$_2$ | H | Cl | Cl |
| 94 | $CH_3$ | $CH_3$ | 4-NO$_2$ | H | F | Cl |
| 95 | $CH_3$ | $CH_3$ | 4-NH$_2$ | H | F | Cl |
| 96 | $CHF_2$ | $CH_3$ | 4-OCH(CH$_3$)CO$_2$C(CH$_3$)$_2$C≡CH | H | F | Cl |
| 97 | $CHF_2$ | $CH_3$ | 4-CN | H | F | Cl |
| 98 | $CHF_2$ | $CH_3$ | 4-NHCH(CH$_3$)CO$_2$C$_2$H$_5$ | H | F | Cl |
| 99 | $CH_3$ | $CH_3$ | 4-OCH(CH$_3$)CO$_2$CH(CH$_3$)$_2$ | H | F | Cl |
| 100 | $CH_3$ | $CH_3$ | 4-OCH(CH$_3$)CO$_2$C$_2$H$_5$ | H | F | Cl |
| 101 | $CHF_2$ | $CH_3$ | 4-OCH(CH$_3$)CO$_2$C(CH$_3$)$_3$ | H | F | Cl |
| 102 | $CHF_2$ | $CH_3$ | 4-OCH$_3$ | H | H | H |
| 103 | $CHF_2$ | $CH_3$ | 4-OCH(CH$_3$)CO$_2$C$_2$H$_5$ | H | H | H |

TABLE 1-continued

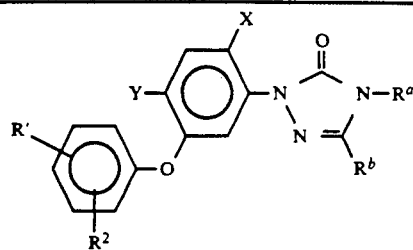

| Cmpd No. | $R^a$ | $R^b$ | $R^2$ | R' | X | Y |
|---|---|---|---|---|---|---|
| 104 | $CHF_2$ | $CH_3$ | 4-$OCH_3$ | H | F | Cl |
| 105 | $CHF_2$ | $CH_3$ | 4-OH | 3-Cl | F | Cl |
| 106 | $CHF_2$ | $CH_3$ | 4-$NO_2$ | 2-Cl | F | Cl |
| 107 | $CHF_2$ | $CH_3$ | 4-$NH_2$ | 2-Cl | F | Cl |
| 108 | $CHF_2$ | $CH_3$ | 4-OH | 2-Cl | F | Cl |
| 109 | $CHF_2$ | $CH_3$ | 4-$NHSO_2C_2H_5$ | H | F | Cl |
| 110 | $CHF_2$ | $CH_3$ | 4-$OCH(CH_3)CO_2CH_3$ | 3-Cl | F | Cl |
| 111 | $CHF_2$ | $CH_3$ | 4-OH | H | Cl | Cl |
| 112 | $CHF_2$ | $CH_3$ | 4-$OCH(CH_3)CO_2CH(CH_3)_2$ | H | Cl | Cl |
| 113 | $CHF_2$ | $CH_3$ | 4-$OCH(CH_3)CO_2CH_3$ | H | Cl | Cl |
| 114 | $CHF_2$ | $CH_3$ | 4-$OCH(CH_3)CO_2H$ | H | Cl | Cl |
| 115 | $CHF_2$ | $CH_3$ | 4-$OCH(CH_3)CO_2^-Na^+$ | H | Cl | Cl |
| 116 | $CHF_2$ | $CH_3$ | 4-$OCH(CH_3)CONHSO_2CH_3$ | H | Cl | Cl |
| 117 | $CHF_2$ | $CH_3$ | 4-$OCH(CH_3)CO_2CH_3$ | 2-F | F | Cl |
| 118 | $CHF_2$ | $CH_3$ | 4-$NO_2$ | 2-F | F | Cl |
| 119 | $CHF_2$ | $CH_3$ | 4-$NH_2$ | 2-F | F | Cl |
| 120 | $CHF_2$ | $CH_3$ | 4-OH | 2-F | F | Cl |
| 121 | $CHF_2$ | $CH_3$ | 4-$NH_2$ | 3-$OCH_3$ | F | Cl |
| 122 | $CHF_2$ | $CH_3$ | 3-$OCH_3$ | H | F | Cl |
| 123 | $CHF_2$ | $CH_3$ | 3-OH | H | F | Cl |
| 124 | $CHF_2$ | $CH_3$ | 3-$OCH(CH_3)CO_2CH_3$ | H | F | Cl |
| 125 | $CHF_2$ | $CH_3$ | 4-$NO_2$ | 3-$OCH_3$ | F | Cl |
| 126 | $CHF_2$ | $CH_3$ | 4-$CO_2CH_3$ | H | F | Cl |
| 127 | $CHF_2$ | $CH_3$ | 4-$CO_2C_2H_5$ | H | F | Cl |
| 128 | $CHF_2$ | $CH_3$ | 4-$CONHSO_2(4-ClC_6H_4)$ | H | F | Cl |
| 129 | $CHF_2$ | $CH_3$ | 4-$CONHSO_2CH_3$ | H | F | Cl |
| 130 | $CHF_2$ | $CH_3$ | 4-$CONHSO_2CH(CH_3)_2$ | H | F | Cl |
| 131 | $CHF_2$ | $CH_3$ | 4-$OC(CH_3)_2C\equiv CH$ | H | F | Cl |
| 132 | $CHF_2$ | $CH_3$ | 4-OH | H | H | H |
| 133 | $CF_2CHF_2$ | $CH_3$ | 4-$OCH(CH_3)CO_2CH_3$ | H | F | Cl |
| 134 | $CF_2CHF_2$ | $CH_3$ | 4-$OCH(CH_3)CO_2CH_3$ | H | Cl | Cl |
| 135 | $CF_2CHF_2$ | $CH_3$ | 4-$OCH(CH_3)CO_2C_2H_5$ | H | F | Cl |
| 136 | $CF_2CHF_2$ | $CH_3$ | 4-OH | H | F | Cl |
| 137 | $CHF_2$ | $CH_3$ | 3-$OCH(CH_3)CO_2CH_3$ | H | Cl | Cl |
| 138 | $CHF_2$ | $CH_3$ | 3-$OCH(CH_3)CO_2CH_3$ | 2-F | Cl | Cl |
| 139 | $CHF_2$ | $CH_3$ | 3-$OCH(CH_3)CO_2C_2H_5$ | H | Cl | Cl |
| 140 | $CHF_2$ | $CH_3$ | 3-$OCH(CH_3)CO_2C_3H_7$ | H | Cl | Cl |
| 141 | $CHF_2$ | $CH_3$ | 3-$OCH(CH_3)CO_2CH(CH_3)_2$ | H | Cl | Cl |
| 142 | $CHF_2$ | $CH_3$ | 3-$OCH(CH_3)CO_2(CH_2)_2O(CH_2)_2OCH_3$ | H | Cl | Cl |
| 143 | $CHF_2$ | $CH_3$ | 3-$OCH(CH_3)CO_2(CH_2)_2OCH_3$ | H | Cl | Cl |
| 144 | $CHF_2$ | $CH_3$ | 3-$OCH_3$ | H | Cl | Cl |
| 145 | $CHF_2$ | $CH_3$ | 4-$OCH(CH_3)CO_2CH_3$ | 2-Cl | F | Cl |
| 146 | $CHF_2$ | $CH_3$ | 4-$OCH(CH_3)CO_2CH(CH_3)_2$ | 2-Cl | F | Cl |
| 147 | $CHF_2$ | $CH_3$ | 4-$OCH(CH_3)CO_2C(CH_3)_3$ | 2-Cl | F | Cl |
| 148 | $CHF_2$ | $CH_3$ | 4-$OCH(CH_3)CO_2H$ | 2-Cl | F | Cl |
| 149 | $CHF_2$ | $CH_3$ | 4-$OCH(CH_3)CO_2C_2H_5$ | 2-Cl | Cl | Cl |
| 150 | $CHF_2$ | $CH_3$ | 4-$OCH(CH_3)CO_2CH_3$ | 2-Cl | Cl | Cl |
| 151 | $CHF_2$ | $CH_3$ | 4-$OCH(CH_3)CO_2C(CH_3)_3$ | 2-Cl | Cl | Cl |
| 152 | $CHF_2$ | $CH_3$ | 4-$OCH_2CO_2CH_3$ | 2-Cl | Cl | Cl |
| 153 | $CHF_2$ | $CH_3$ | 4-$OCH(CH_3)CO_2CH(CH_3)_2$ | 2-Cl | Cl | Cl |
| 154 | $CHF_2$ | $CH_3$ | 4-$OCH(CH_3)CO_2^-Na^+$ | 2-Cl | F | Cl |
| 155 | $CHF_2$ | $CH_3$ | 4-$OCH(CH_3)CO_2C_2H_5$ | 2-F | Cl | Cl |
| 156 | $CHF_2$ | $CH_3$ | 4-$OCH(CH_3)CO_2CH_3$ | 2-F | Cl | Cl |
| 157 | $CHF_2$ | $CH_3$ | 4-$OCH_2CO_2CH_3$ | 2-F | Cl | Cl |
| 158 | $CHF_2$ | $CH_3$ | 4-$OCH_2CO_2CH_3$ | H | Cl | Cl |
| 159 | $CHF_2$ | $CH_3$ | 4-$OCH(CH_3)CO_2(CH_2)_2OCH_3$ | H | Cl | Cl |
| 160 | $CHF_2$ | $CH_3$ | 4-$OCH(CH_3)CO_2CH(CH_3)CH_2OCH_3$ | H | Cl | Cl |
| 161 | $CHF_2$ | $CH_3$ | 4-$OCH(CH_3)CO_2^-NH_2^+(C_2H_5)_2$ | H | Cl | Cl |
| 162 | $CHF_2$ | $CH_3$ | 4-$OCH(CH_3)CO_2^-NH_3^+(CH_2)_{11}CH_3$ | H | Cl | Cl |
| 163 | $CHF_2$ | $CH_3$ | 4-$OCH(CH_3)CO_2C_3H_7$ | H | Cl | Cl |
| 164 | $CHF_2$ | $CH_3$ | 4-$OCH(CH_3)CO_2(CH_2)_2O(CH_2)_2OCH_3$ | H | Cl | Cl |
| 165 | $CHF_2$ | $CH_3$ | 4-$OCH(CH_3)CO_2(CH_2)_3CH_3$ | H | Cl | Cl |
| 166 | $CHF_2$ | $CH_3$ | 4-$OCH(CH_3)CO_2(CH_2)_2O(CH_2)_2OCH_3$ | 2-F | F | Cl |
| 167 | $CHF_2$ | $CH_3$ | 4-$OCH(CH_3)CONH_2$ | H | Cl | Cl |
| 168 | $CHF_2$ | $CH_3$ | 4-$OCH(CH_3)CO_2(CH_2)_2O(CH_2)_2OCH_3$ | 2-F | Cl | Cl |
| 169 | $CHF_2$ | $CH_3$ | 4-$OCH(CH_3)CO_2(CH_2)_2OCH_3$ | H | F | Cl |
| 170 | $CHF_2$ | $CH_3$ | 4-$OCH(CH_3)CO_2(CH_2)_2O(CH_2)_2OCH_3$ | H | F | Cl |
| 171 | $CHF_2$ | $CH_3$ | 4-$OCH_3$ | H | H | Cl |

TABLE 1-continued

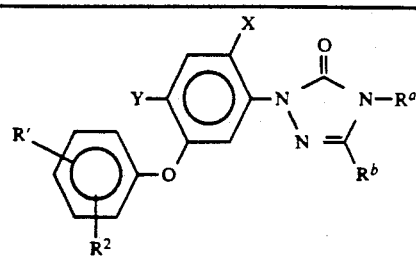

| Cmpd No. | $R^a$ | $R^b$ | $R^2$ | R' | X | Y |
| --- | --- | --- | --- | --- | --- | --- |
| 172 | $CHF_2$ | $CH_3$ | 4-OCH($CH_3$)$CO_2$-cyclopentyl | H | Cl | Cl |
| 173 | $CHF_2$ | $CH_3$ | 4-OCH($CH_3$)CON($C_2H_5$)$_2$ | H | Cl | Cl |
| 174 | $CHF_2$ | $CH_3$ | 4-OCH($CH_3$)$CO_2$($CH_2$)$_{17}CH_3$ | H | Cl | Cl |
| 175 | $CHF_2$ | $CH_3$ | 4-OCH($CH_3$)$CO_2$($CH_2$)$_4CH_3$ | H | Cl | Cl |
| 176 | $CHF_2$ | $CH_3$ | 4-$OCH_3$ | H | Cl | H |
| 177 | $CHF_2$ | $CH_3$ | 4-OCH($CH_3$)$CO_2H$ | H | H | H |
| 178 | $CHF_2$ | $CH_3$ | 3-OH | H | Cl | Cl |
| 179 | $CHF_2$ | $CH_3$ | 4-$NO_2$ | 2-Cl | Cl | Cl |
| 180 | $CHF_2$ | $CH_3$ | 4-$NH_2$ | 2-Cl | Cl | Cl |
| 181 | $CHF_2$ | $CH_3$ | 4-OH | 2-Cl | Cl | Cl |
| 182 | $CHF_2$ | $CH_3$ | 5-OCH($CH_3$)$CO_2CH_3$ | 2-Cl | F | Cl |
| 183 | $CHF_2$ | $CH_3$ | 5-OCH($CH_3$)$CO_2H$ | 2-Cl | F | Cl |
| 184 | $CHF_2$ | $CH_3$ | 5-OCH($CH_3$)$CONH_2$ | 2-Cl | F | Cl |
| 185 | $CHF_2$ | $CH_3$ | 5-OCH($CH_3$)$CO_2CH_3$ | 2-F | F | Cl |
| 186 | $CHF_2$ | $CH_3$ | 5-OCH($CH_3$)$CO_2H$ | 2-F | F | Cl |
| 187 | $CHF_2$ | $CH_3$ | 5-OCH($CH_3$)$CONH_2$ | 2-F | F | Cl |
| 188 | $CHF_2$ | $CH_3$ | 5-OCH($CH_3$)$CO_2CH_3$ | 2-Cl | Cl | Cl |
| 189 | $CHF_2$ | $CH_3$ | 5-OCH($CH_3$)$CO_2C_2H_5$ | 2-Cl | Cl | Cl |
| 190 | $CHF_2$ | $CH_3$ | 5-OCH($CH_3$)$CO_2CH(CH_3)_2$ | 2-Cl | Cl | Cl |
| 191 | $CHF_2$ | $CH_3$ | 5-OCH($CH_3$)$CO_2C_3H_7$ | 2-Cl | Cl | Cl |
| 192 | $CHF_2$ | $CH_3$ | 5-OCH($CH_3$)$CO_2H$ | 2-Cl | Cl | Cl |
| 193 | $CHF_2$ | $CH_3$ | 5-OCH($CH_3$)$CONH_2$ | 2-Cl | Cl | Cl |
| 194 | $CHF_2$ | $CH_3$ | 5-OCH($CH_3$)$CONHCH_3$ | 2-Cl | Cl | Cl |
| 195 | $CHF_2$ | $CH_3$ | 5-OCH($CH_3$)$CON(CH_3)_2$ | 2-Cl | Cl | Cl |
| 196 | $CHF_2$ | $CH_3$ | 5-OCH($CH_3$)$CONHSO_2CH_3$ | 2-Cl | Cl | Cl |
| 197 | $CHF_2$ | $CH_3$ | 5-OCH($CH_3$)$CO_2CH_3$ | 2-F | Cl | Cl |
| 198 | $CHF_2$ | $CH_3$ | 5-OCH($CH_3$)$CO_2C_2H_5$ | 2-F | Cl | Cl |
| 199 | $CHF_2$ | $CH_3$ | 5-OCH($CH_3$)$CO_2C_3H_7$ | 2-F | Cl | Cl |
| 200 | $CHF_2$ | $CH_3$ | 5-$OCH_2CO_2CH_3$ | 2-F | Cl | Cl |
| 201 | $CHF_2$ | $CH_3$ | 5-OCH($CH_3$)$CO_2H$ | 2-F | Cl | Cl |
| 202 | $CHF_2$ | $CH_3$ | 5-OCH($CH_3$)CN | 2-F | Cl | Cl |
| 203 | $CHF_2$ | $CH_3$ | 5-OCH($CH_3$)$CONH_2$ | 2-F | Cl | Cl |
| 204 | $CHF_2$ | $CH_3$ | 5-OCH($CH_3$)$CONHCH_3$ | 2-F | Cl | Cl |
| 205 | $CHF_2$ | $CH_3$ | 5-OCH($CH_3$)$CON(CH_3)_2$ | 2-F | Cl | Cl |
| 206 | $CHF_2$ | $CH_3$ | 5-OCH($CH_3$)$CONHSO_2CH_3$ | 2-F | Cl | Cl |
| 207 | $CHF_2$ | $CH_3$ | 5-OCH($CH_3$)$CONHSO_2CF_3$ | 2-F | Cl | Cl |
| 208 | $CHF_2$ | $CH_3$ | 5-$OCH_2CN$ | 2-F | Cl | Cl |
| 209 | $CHF_2$ | $CH_3$ | 5-OCH($CH_3$)$CO_2CH_2CH_2OCH_3$ | 2-F | Cl | Cl |
| 210 | $CHF_2$ | $CH_3$ | 5-OCH($CH_3$)$CO_2CH(CH_3)CO_2CH_3$ | 2-F | Cl | Cl |
| 211 | $CHF_2$ | $CH_3$ | 5-OCH($CH_3$)$CO_2CH_3$ | 2-Cl,4-$NO_2$ | F | Cl |
| 212 | $CHF_2$ | $CH_3$ | 5-OCH($CH_3$)$CO_2CH_3$ | 2-F,4-$NO_2$ | F | Cl |
| 213 | $CHF_2$ | $CH_3$ | 5-OCH($CH_3$)$CO_2CH_3$ | 2-Cl,4-$NO_2$ | Cl | Cl |
| 214 | $CHF_2$ | $CH_3$ | 5-OCH($CH_3$)$CO_2CH_3$ | 2-F,4-$NO_2$ | Cl | Cl |
| 215 | $CHF_2$ | $CH_3$ | 5-$OCH_3$ | 2-F,4-$NO_2$ | F | Cl |
| 216 | $CHF_2$ | $CH_3$ | 5-$OCH_3$ | 2-F,4-Cl | F | Cl |
| 217 | $CHF_2$ | $CH_3$ | 5-$OCH_3$ | 2-Cl,4-Cl | F | Cl |
| 218 | $CHF_2$ | $CH_3$ | 5-$OCH_3$ | 2-Cl,4-$NO_2$ | Cl | Cl |
| 219 | $CHF_2$ | $CH_3$ | 5-$OCH_3$ | 2-F,4-$NO_2$ | Cl | Cl |
| 220 | $CHF_2$ | $CH_3$ | 5-$OCH_3$ | 2,4-$Cl_2$ | Cl | Cl |
| 221 | $CHF_2$ | $CH_3$ | 3-OCH($CH_3$)$CO_2(CH_2)_3O(CH_2)_3OCH_3$ | H | Cl | Cl |
| 222 | $CHF_2$ | $CH_3$ | 3-OCH($CH_3$)$CO_2[CH_2CH_2OCH_2CH_2O]_2CH_3$ | H | Cl | Cl |
| 223 | $CHF_2$ | $CH_3$ | 3-OCH($CH_3$)$CO_2[CH_2CH_2OCH_2CH_2O]_3CH_3$ | H | Cl | Cl |
| 224 | $CHF_2$ | $CH_3$ | 3-$OCH_2CO_2CH_2CH_2OCH_2CH_2OCH_3$ | H | Cl | Cl |
| 225 | $CHF_2$ | $CH_3$ | 3-OCH($CH_3$)$CO_2(CH_2)_3O(CH_2)_3OCH_3$ | H | F | Cl |
| 226 | $CHF_2$ | $CH_3$ | 3-OCH($CH_3$)$CO_2[CH_2CH_2OCH_2CH_2O]_2CH_3$ | H | F | Cl |
| 227 | $CHF_2$ | $CH_3$ | 4-OCH($CH_3$)$CO_2(CH_2)_3O(CH_2)_3OCH_3$ | H | Cl | Cl |
| 228 | $CHF_2$ | $CH_3$ | 4-OCH($CH_3$)$CO_2[CH_2CH_2OCH_2CH_2O]_2CH_3$ | H | Cl | Cl |
| 229 | $CHF_2$ | $CH_3$ | 4-OCH($CH_3$)$CO_2[CH_2CH_2OCH_2CH_2O]_3CH_3$ | H | Cl | Cl |
| 230 | $CHF_2$ | $CH_3$ | 4-$OCH_2CO_2CH_2CH_2OCH_2CH_2OCH_3$ | H | Cl | Cl |
| 231 | $CHF_2$ | $CH_3$ | 4-OCH($CH_3$)$CO_2(CH_2)_3O(CH_2)_3OCH_3$ | H | F | Cl |
| 232 | $CHF_2$ | $CH_3$ | 4-OCH($CH_3$)$CO_2[CH_2CH_2OCH_2CH_2O]_2CH_3$ | H | F | Cl |

Other representative compounds are identical with the foregoing compounds 1-232, respectively, except that in each case the aromatic ring bearing the R² substituent is a pyridine ring of the formula

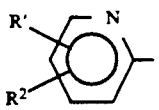

with the R² and R' being in the same positions with respect to the free valence (connected to O) as in said compounds 1-232, see for instance the compounds produced by Examples 3 and 4, and method B above.

TABLE 1A
Pyridinyloxyphenyltriazolinones

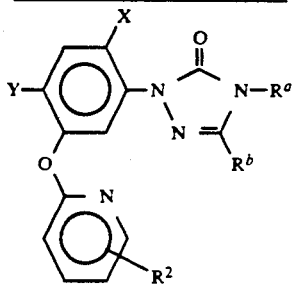

| Cmpd No. | X | Y | R² | R$^a$ | R$^b$ |
|---|---|---|---|---|---|
| A1 | F | Cl | 5-NO₂ | CHF₂ | CH₃ |
| A2 | F | Cl | 5-NH₂ | CHF₂ | CH₃ |
| A3 | F | Cl | 5-NHSO₂(4-ClC₆H₅) | CHF₂ | CH₃ |
| A4 | F | Cl | 5-NHSO₂C₂H₅ | CHF₂ | CH₃ |
| A5 | F | Cl | 5-OH | CHF₂ | CH₃ |
| A6 | F | Cl | 5-OCH(CH₃)CO₂CH₃ | CHF₂ | CH₃ |
| A7 | F | Cl | 5-OCH(CH₃)CO₂C₂H₅ | CHF₂ | CH₃ |
| A8 | F | Cl | 5-OCH(CH₃)CO₂C(CH₃)₃ | CHF₂ | CH₃ |
| A9 | F | Cl | 5-OCH(CH₃)CO₂CH(CH₃)₂ | CHF₂ | CH₃ |
| A10 | F | Cl | 5-OCH(CH₃)CO₂H | CHF₂ | CH₃ |
| A11 | F | Cl | 5-OCH₂C≡CH | CHF₂ | CH₃ |
| A12 | F | Cl | 5-OC(O)CH₃ | CHF₂ | CH₃ |
| A13 | F | Cl | 6-OCH(CH₃)CO₂CH₃ | CHF₂ | CH₃ |
| A14 | F | Cl | 6-OCH(CH₃)CO₂C₂H₅ | CHF₂ | CH₃ |
| A15 | F | Cl | 6-OCH(CH₃)CO₂CH(CH₃)₂ | CHF₂ | CH₃ |

TABLE 1A-continued
Pyridinyloxyphenyltriazolinones

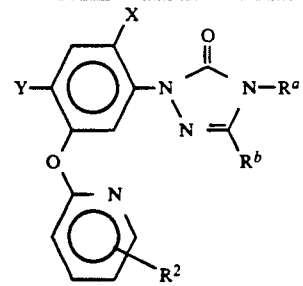

| Cmpd No. | X | Y | R² | R$^a$ | R$^b$ |
|---|---|---|---|---|---|
| A16 | F | Cl | 6-OCH(CH₃)CO₂H | CHF₂ | CH₃ |
| A17 | F | Cl | 6-OCH₂CO₂CH₃ | CHF₂ | CH₃ |
| A18 | F | Cl | 6-OCH₂CN | CHF₂ | CH₃ |
| A19 | F | Cl | 6-OCH(CH₃)CONH₂ | CHF₂ | CH₃ |
| A20 | F | Cl | 6-OCH(CH₃)CONHCH₃ | CHF₂ | CH₃ |
| A21 | F | Cl | 6-OCH(CH₃)CON(CH₃)₂ | CHF₂ | CH₃ |
| A22 | F | Cl | 6-OCH(CH₃)CONHSO₂CH₃ | CHF₂ | CH₃ |
| A23 | F | Cl | 6-OCH(CH₃)CONHSO₂CF₃ | CHF₂ | CH₃ |
| A24 | Cl | Cl | 6-OCH(CH₃)CO₂CH₃ | CHF₂ | CH₃ |
| A25 | Cl | Cl | 6-OCH(CH₃)CO₂H | CHF₂ | CH₃ |
| A26 | Cl | Cl | 6-OCH₂CO₂CH₃ | CHF₂ | CH₃ |
| A27 | Cl | Cl | 6-OCH₂CN | CHF₂ | CH₃ |
| A28 | Cl | Cl | 6-OCH(CH₃)CONH₂ | CHF₂ | CH₃ |
| A29 | Cl | Cl | 6-OCH(CH₃)CONHCH₃ | CHF₂ | CH₃ |
| A30 | Cl | Cl | 6-OCH(CH₃)CON(CH₃)₂ | CHF₂ | CH₃ |

Other representative compounds are identical to the foregoing substituted pyridinyloxy compounds except that the bond from the oxygen to the pyridine ring is at the 3-position or 4-position of the pyridine ring rather than at the 2-position of that ring. In those cases, when the oxygen is at the 3-position, R² is preferably at the 5- or 6-position, and when the oxygen is at the 4-position, R² is preferably at the 2(or 6)-position.

Other representative compounds are identical with the foregoing compounds 1-232, respectively, except that in each case the two benzene rings are connected by sulfur (i.e. Z is sulfur), with the R² and R' being in the same positions with respect to the free valence (connected to S) as in said compounds 1-232.

TABLE 1B

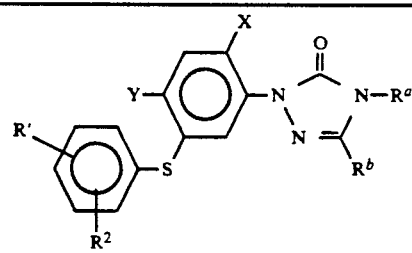

| Cmpd No. | R$^a$ | R$^b$ | R² | R' | X | Y |
|---|---|---|---|---|---|---|
| B1 | CF₂CHF₂ | CH₃ | 4-OCH(CH₃)CO₂CH₃ | H | F | Cl |
| B2 | CF₂CHF₂ | CH₃ | 4-OCH(CH₃)CO₂CH₃ | H | Cl | Cl |
| B3 | CF₂CHF₂ | CH₃ | 4-OCH(CH₃)CO₂C₂H₅ | H | F | Cl |
| B4 | CF₂CHF₂ | CH₃ | 4-OH | H | F | Cl |
| B5 | CHF₂ | CH₃ | 3-OCH(CH₃)CO₂CH₃ | H | Cl | Cl |
| B6 | CHF₂ | CH₃ | 3-OCH(CH₃)CO₂CH₃ | 2-F | Cl | Cl |
| B7 | CHF₂ | CH₃ | 3-OCH(CH₃)CO₂C₂H₅ | H | Cl | Cl |
| B8 | CHF₂ | CH₃ | 3-OCH(CH₃)CO₂C₃H₇ | H | Cl | Cl |
| B9 | CHF₂ | CH₃ | 3-OCH(CH₃)CO₂CH(CH₃)₂ | H | Cl | Cl |
| B10 | CHF₂ | CH₃ | 3-OCH(CH₃)CO₂(CH₂)₂O(CH₂)OCH₃ | H | Cl | Cl |
| B11 | CHF₂ | CH₃ | 3-OCH(CH₃)CO₂(CH₂)₂OCH₃ | H | Cl | Cl |
| B12 | CHF₂ | CH₃ | 3-OCH₃ | H | Cl | Cl |
| B13 | CHF₂ | CH₃ | 4-OCH(CH₃)CO₂CH₃ | 2-Cl | F | Cl |
| B14 | CHF₂ | CH₃ | 4-OCH(CH₃)CO₂CH(CH₃)₂ | 2-Cl | F | Cl |

TABLE 1B-continued

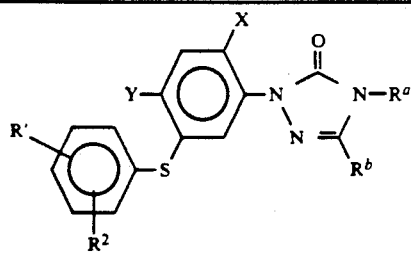

| Cmpd No. | $R^a$ | $R^b$ | $R^2$ | R' | X | Y |
|---|---|---|---|---|---|---|
| B15 | $CHF_2$ | $CH_3$ | 4-$OCH(CH_3)CO_2C(CH_3)_3$ | 2-Cl | F | Cl |
| B16 | $CHF_2$ | $CH_3$ | 4-$OCH(CH_3)CO_2H$ | 2-Cl | F | Cl |
| B17 | $CHF_2$ | $CH_3$ | 4-$OCH(CH_3)CO_2C_2H_5$ | 2-Cl | Cl | Cl |
| B18 | $CHF_2$ | $CH_3$ | 4-$OCH(CH_3)CO_2CH_3$ | 2-Cl | Cl | Cl |
| B19 | $CHF_2$ | $CH_3$ | 4-$OCH(CH_3)CO_2C(CH_3)_3$ | 2-Cl | Cl | Cl |
| B20 | $CHF_2$ | $CH_3$ | 4-$OCH_2CO_2CH_3$ | 2-Cl | Cl | Cl |
| B21 | $CHF_2$ | $CH_3$ | 4-$OCH(CH_3)CO_2CH(CH_3)_2$ | 2-Cl | Cl | Cl |
| B22 | $CHF_2$ | $CH_3$ | 4-$OCH(CH_3)CO_2^-Na^+$ | 2-Cl | F | Cl |
| B23 | $CHF_2$ | $CH_3$ | 4-$OCH(CH_3)CO_2C_2H_5$ | 2-F | Cl | Cl |
| B24 | $CHF_2$ | $CH_3$ | 4-$OCH(CH_3)CO_2CH_3$ | 2-F | Cl | Cl |
| B25 | $CHF_2$ | $CH_3$ | 4-$OCH_2CO_2CH_3$ | 2-F | Cl | Cl |
| B26 | $CHF_2$ | $CH_3$ | 4-$OCH_2CO_2CH_3$ | H | Cl | Cl |
| B27 | $CHF_2$ | $CH_3$ | 4-$OCH(CH_3)CO_2(CH_2)_2OCH_3$ | H | Cl | Cl |
| B28 | $CHF_2$ | $CH_3$ | 4-$OCH(CH_3)CO_2CH(CH_3)CH_2OCH_3$ | H | Cl | Cl |
| B29 | $CHF_2$ | $CH_3$ | 4-$OCH(CH_3)CO_2^-NH_2^+(C_2H_5)_2$ | H | Cl | Cl |
| B30 | $CHF_2$ | $CH_3$ | 4-$OCH(CH_3)CO_2^-NH_3^+(CH_2)_{11}CH_3$ | H | Cl | Cl |
| B31 | $CHF_2$ | $CH_3$ | 4-$OCH(CH_3)CO_2C_3H_7$ | H | Cl | Cl |
| B32 | $CHF_2$ | $CH_3$ | 4-$OCH(CH_3)CO_2(CH_2)_2O(CH_2)_2OCH_3$ | H | Cl | Cl |
| B33 | $CHF_2$ | $CH_3$ | 4-$OCH(CH_3)CO_2(CH_2)_3CH_3$ | H | Cl | Cl |
| B34 | $CHF_2$ | $CH_3$ | 4-$OCH(CH_3)CO_2(CH_2)_2O(CH_2)_2OCH_3$ | 2-F | F | Cl |
| B35 | $CHF_2$ | $CH_3$ | 4-$OCH(CH_3)CONH_2$ | H | Cl | Cl |
| B36 | $CHF_2$ | $CH_3$ | 4-$OCH(CH_3)CO_2(CH_2)_2O(CH_2)_2OCH_3$ | 2-F | Cl | Cl |
| B37 | $CHF_2$ | $CH_3$ | 4-$OCH(CH_3)CO_2(CH_2)_2OCH_3$ | H | F | Cl |
| B38 | $CHF_2$ | $CH_3$ | 4-$OCH(CH_3)CO_2(CH_2)_2O(CH_2)_2OCH_3$ | H | F | Cl |
| B39 | $CHF_2$ | $CH_3$ | 4-$OCH_3$ | H | H | Cl |
| B40 | $CHF_2$ | $CH_3$ | 4-$OCH(CH_3)CO_2$-cyclopentyl | H | Cl | Cl |
| B41 | $CHF_2$ | $CH_3$ | 4-$OCH(CH_3)CON(C_2H_5)_2$ | H | Cl | Cl |
| B42 | $CHF_2$ | $CH_3$ | 4-$OCH(CH_3)CO_2(CH_2)_{17}CH_3$ | H | Cl | Cl |
| B43 | $CHF_2$ | $CH_3$ | 4-$OCH(CH_3)CO_2(CH_2)_4CH_3$ | H | Cl | Cl |
| B44 | $CHF_2$ | $CH_3$ | 4-$OCH_3$ | H | Cl | H |
| B45 | $CHF_2$ | $CH_3$ | 4-$OCH(CH_3)CO_2H$ | H | H | H |
| B46 | $CHF_2$ | $CH_3$ | 3-OH | H | Cl | Cl |
| B47 | $CHF_2$ | $CH_3$ | 4-$NO_2$ | 2-Cl | Cl | Cl |
| B48 | $CHF_2$ | $CH_3$ | 4-$NH_2$ | 2-Cl | Cl | Cl |
| B49 | $CHF_2$ | $CH_3$ | 4-OH | 2-Cl | Cl | Cl |
| B50 | $CHF_2$ | $CH_3$ | 5-$OCH(CH_3)CO_2CH_3$ | 2-Cl | F | Cl |
| B51 | $CHF_2$ | $CH_3$ | 5-$OCH(CH_3)CO_2H$ | 2-Cl | F | Cl |
| B52 | $CHF_2$ | $CH_3$ | 5-$OCH(CH_3)CONH_2$ | 2-Cl | F | Cl |
| B53 | $CHF_2$ | $CH_3$ | 5-$OCH(CH_3)CO_2CH_3$ | 2-F | F | Cl |
| B54 | $CHF_2$ | $CH_3$ | 5-$OCH(CH_3)CO_2H$ | 2-F | F | Cl |
| B55 | $CHF_2$ | $CH_3$ | 5-$OCH(CH_3)CONH_2$ | 2-F | F | Cl |
| B56 | $CHF_2$ | $CH_3$ | 5-$OCH(CH_3)CO_2CH_3$ | 2-Cl | Cl | Cl |
| B57 | $CHF_2$ | $CH_3$ | 5-$OCH(CH_3)CO_2C_2H_5$ | 2-Cl | Cl | Cl |
| B58 | $CHF_2$ | $CH_3$ | 5-$OCH(CH_3)CO_2CH(CH_3)_2$ | 2-Cl | Cl | Cl |
| B59 | $CHF_2$ | $CH_3$ | 5-$OCH(CH_3)CO_2C_3H_7$ | 2-Cl | Cl | Cl |
| B60 | $CHF_2$ | $CH_3$ | 5-$OCH(CH_3)CO_2H$ | 2-Cl | Cl | Cl |
| B61 | $CHF_2$ | $CH_3$ | 5-$OCH(CH_3)CONH_2$ | 2-Cl | Cl | Cl |
| B62 | $CHF_2$ | $CH_3$ | 5-$OCH(CH_3)CONHCH_3$ | 2-Cl | Cl | Cl |
| B63 | $CHF_2$ | $CH_3$ | 5-$OCH(CH_3)CON(CH_3)_2$ | 2-Cl | Cl | Cl |
| B64 | $CHF_2$ | $CH_3$ | 5-$OCH(CH_3)CONHSO_2CH_3$ | 2-Cl | Cl | Cl |
| B65 | $CHF_2$ | $CH_3$ | 5-$OCH(CH_3)CO_2CH_3$ | 2-F | Cl | Cl |
| B66 | $CHF_2$ | $CH_3$ | 5-$OCH(CH_3)CO_2C_2H_5$ | 2-F | Cl | Cl |
| B67 | $CHF_2$ | $CH_3$ | 5-$OCH(CH_3)CO_2C_3H_7$ | 2-F | Cl | Cl |
| B68 | $CHF_2$ | $CH_3$ | 5-$OCH_2CO_2CH_3$ | 2-F | Cl | Cl |
| B69 | $CHF_2$ | $CH_3$ | 5-$OCH(CH_3)CO_2H$ | 2-F | Cl | Cl |
| B70 | $CHF_2$ | $CH_3$ | 5-$OCH(CH_3)CN$ | 2-F | Cl | Cl |
| B71 | $CHF_2$ | $CH_3$ | 5-$OCH(CH_3)CONH_2$ | 2-F | Cl | Cl |
| B72 | $CHF_2$ | $CH_3$ | 5-$OCH(CH_3)CONHCH_3$ | 2-F | Cl | Cl |
| B73 | $CHF_2$ | $CH_3$ | 5-$OCH(CH_3)CON(CH_3)_2$ | 2-F | Cl | Cl |
| B74 | $CHF_2$ | $CH_3$ | 5-$OCH(CH_3)CONHSO_2CH_3$ | 2-F | Cl | Cl |
| B75 | $CHF_2$ | $CH_3$ | 5-$OCH(CH_3)CONHSO_2CF_3$ | 2-F | Cl | Cl |

TABLE 1B-continued

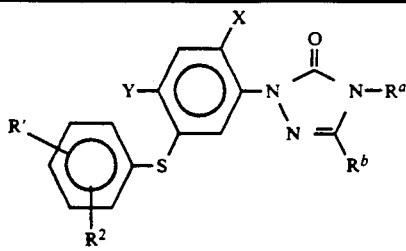

| Cmpd No. | $R^a$ | $R^b$ | $R^2$ | R' | X | Y |
|---|---|---|---|---|---|---|
| B76 | $CHF_2$ | $CH_3$ | 5-$OCH_2CN$ | 2-F | Cl | Cl |
| B77 | $CHF_2$ | $CH_3$ | 5-$OCH(CH_3)CO_2CH_2CH_2OCH_3$ | 2-F | Cl | Cl |
| B78 | $CHF_2$ | $CH_3$ | 5-$OCH(CH_3)CO_2CH(CH_3)CO_2CH_3$ | 2-F | Cl | Cl |
| B79 | $CHF_2$ | $CH_3$ | 5-$OCH(CH_3)CO_2CH_3$ | 2-Cl, 4-$NO_2$ | F | Cl |
| B80 | $CHF_2$ | $CH_3$ | 5-$OCH(CH_3)CO_2CH_3$ | 2-F, 4-$NO_2$ | F | Cl |
| B81 | $CHF_2$ | $CH_3$ | 5-$OCH(CH_3)CO_2CH_3$ | 2-Cl, 4-$NO_2$ | Cl | Cl |
| B82 | $CHF_2$ | $CH_3$ | 5-$OCH(CH_3)CO_2CH_3$ | 2-F, 4-$NO_2$ | Cl | Cl |
| B83 | $CHF_2$ | $CH_3$ | 5-$OCH_3$ | 2-F, 4-$NO_2$ | F | Cl |
| B84 | $CHF_2$ | $CH_3$ | 5-$OCH_3$ | 2-F, 4-Cl | F | Cl |
| B85 | $CHF_2$ | $CH_3$ | 5-$OCH_3$ | 2-Cl, 4-Cl | F | Cl |
| B86 | $CHF_2$ | $CH_3$ | 5-$OCH_3$ | 2-Cl, 4-$NO_2$ | Cl | Cl |
| B87 | $CHF_2$ | $CH_3$ | 5-$OCH_3$ | 2-F, 4-$NO_2$ | Cl | Cl |
| B88 | $CHF_2$ | $CH_3$ | 5-$OCH_3$ | 2,4-$Cl_2$ | Cl | Cl |
| B89 | $CHF_2$ | $CH_3$ | 4-$OCH(CH_3)CO_2CH_3$ | H | Cl | Cl |
| B90 | $CHF_2$ | $CH_3$ | 4-$OCH(CH_3)CO_2C_2H_5$ | H | Cl | Cl |

Other representative compounds are identical with the foregoing compounds 1-232, respectively, except that in each case the two benzene rings are connected by $NR^c$ (i.e. Z is $NR^c$), $R^c$ being hydrogen or lower alkyl, with the $R^2$ and R' being in the same positions with respect to the free valence (connected to $NR^c$) as in said compounds 1-232.

TABLE 1C

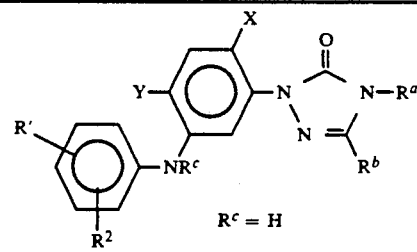

$R^c$ = H

| Cmpd No. | $R^a$ | $R^b$ | $R^2$ | R' | X | Y |
|---|---|---|---|---|---|---|
| C1 | $CF_2CHF_2$ | $CH_3$ | 4-$OCH(CH_3)CO_2CH_3$ | H | F | Cl |
| C2 | $CF_2CHF_2$ | $CH_3$ | 4-$OCH(CH_3)CO_2CH_3$ | H | Cl | Cl |
| C3 | $CF_2CHF_2$ | $CH_3$ | 4-$OCH(CH_3)CO_2C_2H_5$ | H | F | Cl |
| C4 | $CF_2CHF_2$ | $CH_3$ | 4-OH | H | F | Cl |
| C5 | $CHF_2$ | $CH_3$ | 3-$OCH(CH_3)CO_2CH_3$ | H | Cl | Cl |
| C6 | $CHF_2$ | $CH_3$ | 3-$OCH(CH_3)CO_2CH_3$ | 2-F | Cl | Cl |
| C7 | $CHF_2$ | $CH_3$ | 3-$OCH(CH_3)CO_2C_2H_5$ | H | Cl | Cl |
| C8 | $CHF_2$ | $CH_3$ | 3-$OCH(CH_3)CO_2C_3H_7$ | H | Cl | Cl |
| C9 | $CHF_2$ | $CH_3$ | 3-$OCH(CH_3)CO_2CH(CH_3)_2$ | H | Cl | Cl |
| C10 | $CHF_2$ | $CH_3$ | 3-$OCH(CH_3)CO_2(CH_2)_2O(CH_2)_2OCH_3$ | H | Cl | Cl |
| C11 | $CHF_2$ | $CH_3$ | 3-$OCH(CH_3)CO_2(CH_2)_2OCH_3$ | H | Cl | Cl |
| C12 | $CHF_2$ | $CH_3$ | 3-$OCH_3$ | H | Cl | Cl |
| C13 | $CHF_2$ | $CH_3$ | 4-$OCH(CH_3)CO_2CH_3$ | 2-Cl | F | Cl |
| C14 | $CHF_2$ | $CH_3$ | 4-$OCH(CH_3)CO_2CH_2CH_3$ | 2-Cl | F | Cl |
| C15 | $CHF_2$ | $CH_3$ | 4-$OCH(CH_3)CO_2C(CH_3)_3$ | 2-Cl | F | Cl |
| C16 | $CHF_2$ | $CH_3$ | 4-$OCH(CH_3)CO_2H$ | 2-Cl | F | Cl |
| C17 | $CHF_2$ | $CH_3$ | 4-$OCH(CH_3)CO_2C_2H_5$ | 2-Cl | Cl | Cl |
| C18 | $CHF_2$ | $CH_3$ | 4-$OCH(CH_3)CO_2CH_3$ | 2-Cl | Cl | Cl |
| C19 | $CHF_2$ | $CH_3$ | 4-$OCH(CH_3)CO_2C(CH_3)_3$ | 2-Cl | Cl | Cl |
| C20 | $CHF_2$ | $CH_3$ | 4-$OCH_2CO_2CH_3$ | 2-Cl | Cl | Cl |
| C21 | $CHF_2$ | $CH_3$ | 4-$OCH(CH_3)CO_2CH(CH_3)_2$ | 2-Cl | Cl | Cl |
| C22 | $CHF_2$ | $CH_3$ | 4-$OCH(CH_3)CO_2^-Na^+$ | 2-Cl | F | Cl |
| C23 | $CHF_2$ | $CH_3$ | 4-$OCH(CH_3)CO_2C_2H_5$ | 2-F | Cl | Cl |
| C24 | $CHF_2$ | $CH_3$ | 4-$OCH(CH_3)CO_2CH_3$ | 2-F | Cl | Cl |
| C25 | $CHF_2$ | $CH_3$ | 4-$OCH_2CO_2CH_3$ | 2-F | Cl | Cl |
| C26 | $CHF_2$ | $CH_3$ | 4-$OCH_2CO_2CH_3$ | H | Cl | Cl |
| C27 | $CHF_2$ | $CH_3$ | 4-$OCH(CH_3)CO_2(CH_2)_2OCH_3$ | H | Cl | Cl |
| C28 | $CHF_2$ | $CH_3$ | 4-$OCH(CH_3)CO_2CH(CH_3)CH_2OCH_3$ | H | Cl | Cl |
| C29 | $CHF_2$ | $CH_3$ | 4-$OCH(CH_3)CO_2^-NH_2^+(C_2H_5)_2$ | H | Cl | Cl |

TABLE 1C-continued

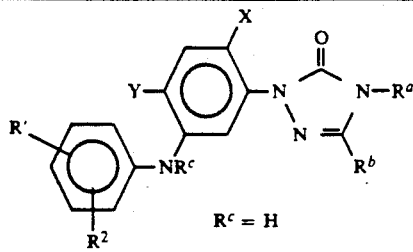

Rᶜ = H

| Cmpd No. | Rᵃ | Rᵇ | R² | R' | X | Y |
|---|---|---|---|---|---|---|
| C30 | CHF₂ | CH₃ | 4-OCH(CH₃)CO₂⁻NH₃⁺(CH₂)₁₁CH₃ | H | Cl | Cl |
| C31 | CHF₂ | CH₃ | 4-OCH(CH₃)CO₂C₃H₇ | H | Cl | Cl |
| C32 | CHF₂ | CH₃ | 4-OCH(CH₃)CO₂(CH₂)₂O(CH₂)₂OCH₃ | H | Cl | Cl |
| C33 | CHF₂ | CH₃ | 4-OCH(CH₃)CO₂(CH₂)₃CH₃ | H | Cl | Cl |
| C34 | CHF₂ | CH₃ | 4-OCH(CH₃)CO₂(CH₂)₂O(CH₂)₂OCH₃ | 2-F | F | Cl |
| C35 | CHF₂ | CH₃ | 4-OCH(CH₃)CONH₂ | H | Cl | Cl |
| C36 | CHF₂ | CH₃ | 4-OCH(CH₃)CO₂(CH₂)₂O(CH₂)₂OCH₃ | 2-F | Cl | Cl |
| C37 | CHF₂ | CH₃ | 4-OCH(CH₃)CO₂(CH₂)₂OCH₃ | H | F | Cl |
| C38 | CHF₂ | CH₃ | 4-OCH(CH₃)CO₂(CH₂)₂O(CH₂)₂OCH₃ | H | F | Cl |
| C39 | CHF₂ | CH₃ | 4-OCH₃ | H | H | Cl |
| C40 | CHF₂ | CH₃ | 4-OCH(CH₃)CO₂-cyclopentyl | H | Cl | Cl |
| C41 | CHF₂ | CH₃ | 4-OCH(CH₃)CON(C₂H₅)₂ | H | Cl | Cl |
| C42 | CHF₂ | CH₃ | 4-OCH(CH₃)CO₂(CH₂)₁₇CH₃ | H | Cl | Cl |
| C43 | CHF₂ | CH₃ | 4-OCH(CH₃)CO₂(CH₂)₄CH₃ | H | Cl | Cl |
| C44 | CHF₂ | CH₃ | 4-OCH₃ | H | Cl | H |
| C45 | CHF₂ | CH₃ | 4-OCH(CH₃)CO₂H | H | H | H |
| C46 | CHF₂ | CH₃ | 3-OH | H | Cl | Cl |
| C47 | CHF₂ | CH₃ | 4-NO₂ | 2-Cl | Cl | Cl |
| C48 | CHF₂ | CH₃ | 4-NH₂ | 2-Cl | Cl | Cl |
| C49 | CHF₂ | CH₃ | 4-OH | 2-Cl | Cl | Cl |
| C50 | CHF₂ | CH₃ | 5-OCH(CH₃)CO₂CH₃ | 2-Cl | F | Cl |
| C51 | CHF₂ | CH₃ | 5-OCH(CH₃)CO₂H | 2-Cl | F | Cl |
| C52 | CHF₂ | CH₃ | 5-OCH(CH₃)CONH₂ | 2-Cl | F | Cl |
| C53 | CHF₂ | CH₃ | 5-OCH(CH₃)CO₂CH₃ | 2-F | F | Cl |
| C54 | CHF₂ | CH₃ | 5-OCH(CH₃)CO₂H | 2-F | F | Cl |
| C55 | CHF₂ | CH₃ | 5-OCH(CH₃)CONH₂ | 2-F | F | Cl |
| C56 | CHF₂ | CH₃ | 5-OCH(CH₃)CO₂CH₃ | 2-Cl | Cl | Cl |
| C57 | CHF₂ | CH₃ | 5-OCH(CH₃)CO₂C₂H₅ | 2-Cl | Cl | Cl |
| C58 | CHF₂ | CH₃ | 5-OCH(CH₃)CO₂CH(CH₃)₂ | 2-Cl | Cl | Cl |
| C59 | CHF₂ | CH₃ | 5-OCH(CH₃)CO₂C₃H₇ | 2-Cl | Cl | Cl |
| C60 | CHF₂ | CH₃ | 5-OCH(CH₃)CO₂H | 2-Cl | Cl | Cl |
| C61 | CHF₂ | CH₃ | 5-OCH(CH₃)CONH₂ | 2-Cl | Cl | Cl |
| C62 | CHF₂ | CH₃ | 5-OCH(CH₃)CONHCH₃ | 2-Cl | Cl | Cl |
| C63 | CHF₂ | CH₃ | 5-OCH(CH₃)CON(CH₃)₂ | 2-Cl | Cl | Cl |
| C64 | CHF₂ | CH₃ | 5-OCH(CH₃)CONHSO₂CH₃ | 2-Cl | Cl | Cl |
| C65 | CHF₂ | CH₃ | 5-OCH(CH₃)CO₂CH₃ | 2-F | Cl | Cl |
| C66 | CHF₂ | CH₃ | 5-OCH(CH₃)CO₂C₂H₅ | 2-F | Cl | Cl |
| C67 | CHF₂ | CH₃ | 5-OCH(CH₃)CO₂C₃H₇ | 2-F | Cl | Cl |
| C68 | CHF₂ | CH₃ | 5-OCH₂CO₂CH₃ | 2-F | Cl | Cl |
| C69 | CHF₂ | CH₃ | 5-OCH(CH₃)CO₂H | 2-F | Cl | Cl |
| C70 | CHF₂ | CH₃ | 5-OCH(CH₃)CN | 2-F | Cl | Cl |
| C71 | CHF₂ | CH₃ | 5-OCH(CH₃)CONH₂ | 2-F | Cl | Cl |
| C72 | CHF₂ | CH₃ | 5-OCH(CH₃)CONHCH₃ | 2-F | Cl | Cl |
| C73 | CHF₂ | CH₃ | 5-OCH(CH₃)CON(CH₃)₂ | 2-F | Cl | Cl |
| C74 | CHF₂ | CH₃ | 5-OCH(CH₃)CONHSO₂CH₃ | 2-F | Cl | Cl |
| C75 | CHF₂ | CH₃ | 5-OCH(CH₃)CONHSO₂CF₃ | 2-F | Cl | Cl |
| C76 | CHF₂ | CH₃ | 5-OCH₂CN | 2-F | Cl | Cl |
| C77 | CHF₂ | CH₃ | 5-OCH(CH₃)CO₂CH₂CH₂OCH₃ | 2-F | Cl | Cl |
| C78 | CHF₂ | CH₃ | 5-OCH(CH₃)CO₂CH(CH₃)CO₂CH₃ | 2-F | Cl | Cl |
| C79 | CHF₂ | CH₃ | 5-OCH(CH₃)CO₂CH₃ | 2-Cl, 4-NO₂ | F | Cl |
| C80 | CHF₂ | CH₃ | 5-OCH(CH₃)CO₂CH₃ | 2-F, 4-NO₂ | F | Cl |
| C81 | CHF₂ | CH₃ | 5-OCH(CH₃)CO₂CH₃ | 2-Cl, 4-NO₂ | Cl | Cl |
| C82 | CHF₂ | CH₃ | 5-OCH(CH₃)CO₂CH₃ | 2-F, 4-NO₂ | Cl | Cl |
| C83 | CHF₂ | CH₃ | 5-OCH₃ | 2-F, 4-NO₂ | F | Cl |
| C84 | CHF₂ | CH₃ | 5-OCH₃ | 2-F, 4-Cl | F | Cl |
| C85 | CHF₂ | CH₃ | 5-OCH₃ | 2-Cl, 4-Cl | F | Cl |
| C86 | CHF₂ | CH₃ | 5-OCH₃ | 2-Cl, 4-NO₂ | Cl | Cl |
| C87 | CHF₂ | CH₃ | 5-OCH₃ | 2-F, 4-NO₂ | Cl | Cl |
| C88 | CHF₂ | CH₃ | 5-OCH₃ | 2,4-Cl₂ | Cl | Cl |
| C89 | CHF₂ | CH₃ | NO₂ | H | Cl | Cl |

TABLE 1C-continued

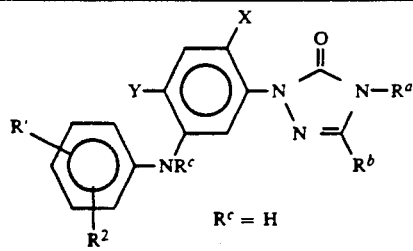

$R^c = H$

| Cmpd No. | $R^a$ | $R^b$ | $R^2$ | $R'$ | X | Y |
|---|---|---|---|---|---|---|
| C90 | CHF$_2$ | CH$_3$ | NH$_2$ | H | Cl | Cl |

| Cmpd No. | M.P. (°C.) | Empirical Formula | Elemental Analysis C | H | N | Cmpd No. | M.P. (°C.) | Empirical Formula | Elemental Analysis C | H | N |
|---|---|---|---|---|---|---|---|---|---|---|---|
| 1 | 164–165.5 | C$_{17}$H$_9$ClF$_3$N$_5$O$_4$ | C 46.43 | 2.06 | 15.93 | 111 | 127–128 | C$_{16}$H$_{11}$Cl$_2$F$_2$N$_3$O$_3$ | | | |
| | | | F 46.60 | 2.28 | 15.84 | 112 | 121–124 | C$_{22}$H$_{21}$Cl$_2$F$_2$N$_3$O$_5$ | C 51.17 | 4.10 | 8.14 |
| 2 | 162–165 | C$_{16}$H$_{11}$ClF$_3$N$_3$O$_3$ | | | | | | | F 50.34 | 4.41 | 8.49 |
| 3 | 133–135 | C$_{16}$H$_{12}$ClF$_3$N$_4$O$_2$ | | | | 113 | 120–121 | C$_{20}$H$_{17}$Cl$_2$F$_2$N$_3$O$_5$ | C 49.19 | 3.51 | 8.61 |
| 4 | 115–117 | C$_{16}$H$_{10}$ClF$_3$N$_4$O$_4$ | | | | | | | F 48.81 | 3.32 | 8.53 |
| 5 | 128–129 | C$_{21}$H$_{19}$ClF$_3$N$_3$O$_5$ | C 51.91 | 3.94 | 8.65 | 114 | 185–186 | C$_{19}$H$_{15}$Cl$_2$F$_2$N$_3$O$_5$ | C 48.12 | 3.19 | 8.86 |
| | | | F 51.81 | 3.69 | 8.79 | | | | F 48.40 | 3.17 | 8.62 |
| 6 | 86–88 | C$_{19}$H$_{13}$ClF$_3$N$_3$O$_3$ | C 53.84 | 3.09 | 9.91 | 115 | 160 (dec) | C$_{19}$H$_{14}$Cl$_2$F$_2$N$_3$NaO$_5$ | | | |
| | | | F 53.43 | 3.07 | 9.80 | 116 | 150–152 | C$_{20}$H$_{18}$Cl$_2$F$_2$N$_4$O$_6$S | C 43.57 | 3.29 | 10.15 |
| 7 | 136–138 | C$_{20}$H$_{17}$ClF$_3$N$_3$O$_5$ | C 50.89 | 3.64 | 8.91 | | | | F 44.48 | 3.45 | 9.07 |
| | | | F 50.58 | 3.53 | 8.78 | 117 | oil | C$_{20}$H$_{16}$ClF$_4$N$_3$O$_5$ | | | |
| 32 | oil | C$_{20}$H$_{18}$ClF$_3$N$_4$O$_6$S | | | | 118 | 123–125 | C$_{16}$H$_9$ClF$_4$N$_4$O$_4$ | | | |
| 91 | 113.5–115 | C$_{22}$H$_{21}$ClF$_3$N$_3$O$_5$ | | | | 119 | 149–151 | C$_{16}$H$_{11}$ClF$_4$N$_4$O$_2$ | | | |
| 92 | thick oil | C$_{16}$H$_{10}$Cl$_2$F$_2$N$_4$O$_4$ | | | | 120 | 155–156 | C$_{16}$H$_{10}$ClF$_4$N$_3$O$_3$ | | | |
| 27 | 119–120 | C$_{19}$H$_{16}$ClF$_3$N$_4$O$_4$ | C 49.95 | 3.53 | 12.26 | 121 | oil | C$_{17}$H$_{14}$ClF$_3$N$_4$O$_3$ | | | |
| | | | F 49.80 | 3.48 | 12.54 | 122 | oil | C$_{17}$H$_{13}$ClF$_3$N$_3$O$_3$ | | | |
| 29 | 130–132 | C$_{21}$H$_{20}$ClF$_3$N$_4$O$_4$ | C 52.02 | 4.16 | 11.56 | 123 | oil | C$_{16}$H$_{11}$ClF$_3$N$_3$O$_3$ | | | |
| | | | F 51.71 | 4.26 | 11.33 | 124 | oil | C$_{20}$H$_{17}$ClF$_3$N$_3$O$_3$ | | | |
| 43 | 156.5–158 | C$_{19}$H$_{15}$ClF$_3$N$_3$O$_2$ | C 49.85 | 3.30 | 9.18 | 125 | 127–128 | C$_{17}$H$_{12}$ClF$_3$N$_4$O$_5$ | | | |
| | | | F 49.76 | 3.60 | 8.64 | 126 | 97–98 | C$_{18}$H$_{13}$ClF$_3$N$_3$O$_4$ | C 50.54 | 3.06 | 9.82 |
| 44 | oil | C$_{20}$H$_{17}$ClF$_3$N$_3$O$_5$ | C 50.91 | 3.64 | 8.91 | | | | F 50.69 | 3.01 | 9.99 |
| | | | F 50.62 | 3.77 | 8.84 | 127 | 79–81 | C$_{19}$H$_{15}$ClF$_3$N$_3$O$_4$ | C 51.65 | 3.43 | 9.51 |
| 46 | oil | C$_{19}$H$_{14}$ClF$_3$N$_4$O$_3$ | C 52.00 | 3.22 | 12.77 | | | | F 51.40 | 3.58 | 9.71 |
| | | | F 51.95 | 3.39 | 12.23 | 128 | 99–100 | C$_{23}$H$_{15}$Cl$_2$F$_3$N$_4$O$_5$S | C 47.02 | 2.58 | 9.54 |
| 49 | oil | C$_{21}$H$_{19}$ClF$_3$N$_3$O$_5$ | | | | | | | F 47.30 | 2.72 | 9.28 |
| 54 | oil | C$_{21}$H$_{18}$Cl$_2$F$_3$N$_3$O$_5$ | | | | 129 | 102–104 | C$_{18}$H$_{14}$ClF$_3$N$_4$O$_5$S | C 44.04 | 2.88 | 11.41 |
| 55 | oil | C$_{21}$H$_{18}$ClF$_4$N$_3$O$_5$ | | | | | | | F 45.04 | 2.79 | 10.86 |
| 56 | oil | C$_{21}$H$_{18}$Cl$_2$F$_3$N$_3$O$_5$ | | | | 130 | 185–187 | C$_{20}$H$_{18}$ClF$_3$N$_4$O$_5$S | C 46.29 | 3.50 | 10.80 |
| 66 | 111–112 | C$_{21}$H$_{18}$ClF$_3$N$_4$O$_7$ | | | | | | | F 46.11 | 3.41 | 10.73 |
| 82 | oil | C$_{21}$H$_{19}$Cl$_2$F$_2$N$_3$O$_5$ | C 50.21 | 3.82 | 8.37 | 131 | oil | C$_{21}$H$_{17}$ClF$_3$N$_3$O$_3$ | C 55.82 | 3.80 | 9.30 |
| | | | F 51.37 | 3.95 | 8.66 | | | | F 55.61 | 3.69 | 9.34 |
| 93 | 56–59 | C$_{16}$H$_{12}$Cl$_2$F$_2$N$_4$O$_2$ | | | | 132 | 150–152 | C$_{16}$H$_{13}$F$_2$N$_3$O$_3$ | | | |
| 94 | 117–120 | C$_{16}$H$_{12}$ClFN$_4$O$_4$ | | | | 137 | oil | C$_{20}$H$_{17}$Cl$_2$F$_2$N$_3$O$_5$ | | | |
| 95 | 155–158 | C$_{16}$H$_{14}$ClFN$_4$O$_2$ | | | | 138 | oil | C$_{20}$H$_{16}$Cl$_2$F$_3$N$_3$O$_5$ | | | |
| 96 | oil | C$_{24}$H$_{21}$ClF$_3$N$_3$O$_5$ | C 55.02 | 4.05 | 8.02 | 139 | oil | C$_{21}$H$_{19}$Cl$_2$F$_2$N$_3$O$_5$ | | | |
| | | | F 55.52 | 4.23 | 7.48 | 140 | oil | C$_{22}$H$_{21}$Cl$_2$F$_2$N$_3$O$_5$ | | | |
| 97 | 175–177 | C$_{17}$H$_{10}$ClF$_3$N$_4$O$_2$ | C 51.72 | 2.55 | 14.19 | 141 | oil | C$_{22}$H$_{21}$Cl$_2$F$_2$N$_3$O$_5$ | | | |
| | | | F 51.43 | 2.62 | 13.90 | 142 | oil | C$_{24}$H$_{25}$Cl$_2$F$_2$N$_3$O$_7$ | | | |
| 98 | oil | C$_{21}$H$_{20}$ClF$_3$N$_4$O$_4$ | C 52.02 | 4.17 | 11.56 | 143 | oil | C$_{22}$H$_{21}$Cl$_2$F$_2$N$_3$O$_6$ | | | |
| | | | F 53.85 | 4.19 | 10.71 | 144 | oil | C$_{17}$H$_{13}$Cl$_2$F$_2$N$_3$O$_3$ | | | |
| 99 | oil | C$_{22}$H$_{23}$ClFN$_3$O$_5$ | C 56.96 | 5.00 | 9.06 | 145 | oil | C$_{20}$H$_{16}$Cl$_2$F$_3$N$_3$O$_5$ | | | |
| | | | F 57.00 | 4.74 | 8.78 | 146 | oil | C$_{22}$H$_{20}$Cl$_2$F$_3$N$_3$O$_5$ | | | |
| 100 | oil | C$_{21}$H$_{21}$ClFN$_3$O$_5$ | C 56.06 | 4.20 | 9.34 | 147 | oil | C$_{23}$H$_{22}$Cl$_2$F$_3$N$_3$O$_5$ | | | |
| | | | F 56.28 | 4.47 | 9.27 | 148 | oil | C$_{19}$H$_{14}$Cl$_2$F$_3$N$_3$O$_5$ | | | |
| 101 | 115–117.5 | C$_{23}$H$_{23}$ClF$_3$N$_3$O$_5$ | C 53.75 | 4.51 | 8.18 | 149 | oil | C$_{21}$H$_{18}$Cl$_3$F$_2$N$_3$O$_5$ | | | |
| | | | F 52.98 | 4.31 | 7.88 | 150 | oil | C$_{20}$H$_{16}$Cl$_3$F$_2$N$_3$O$_5$ | | | |
| 102 | 73–75 | C$_{17}$H$_{15}$F$_2$N$_3$O$_3$ | | | | 151 | oil | C$_{23}$H$_{22}$Cl$_3$F$_2$N$_3$O$_5$ | | | |
| 103 | oil | C$_{21}$H$_{21}$F$_2$N$_3$O$_5$ | C 58.24 | 4.88 | 9.69 | 152 | oil | C$_{19}$H$_{14}$Cl$_3$F$_2$N$_3$O$_5$ | | | |
| | | | F 58.20 | 4.91 | 7.98 | 153 | oil | C$_{22}$H$_{20}$Cl$_3$F$_2$N$_3$O$_5$ | | | |
| 104 | oil | C$_{17}$H$_{13}$ClF$_3$N$_3$O$_3$ | C 51.07 | 3.28 | 10.51 | 154 | 139–141 | C$_{19}$H$_{13}$Cl$_2$F$_3$N$_3$NaO$_5$ | | | |
| | | | F 50.31 | 3.05 | 10.32 | 155 | oil | C$_{21}$H$_{18}$Cl$_2$F$_2$N$_3$O$_5$ | | | |
| 105 | 139–140 | C$_{16}$H$_{10}$Cl$_2$F$_3$N$_3$O$_3$ | | | | 156 | oil | C$_{20}$H$_{16}$Cl$_2$F$_3$N$_3$O$_5$ | | | |
| 106 | 140–141 | C$_{16}$H$_9$Cl$_2$F$_3$N$_4$O$_4$ | | | | 157 | oil | C$_{19}$H$_{14}$Cl$_2$F$_3$N$_3$O$_5$ | | | |
| 107 | 112–115 | C$_{16}$H$_{11}$Cl$_2$F$_3$N$_4$O$_2$ | | | | 158 | 126.5–127.5 | C$_{19}$H$_{15}$Cl$_2$F$_2$N$_3$O$_5$ | | | |
| 108 | 156–157 | C$_{16}$H$_{10}$Cl$_2$F$_3$N$_3$O$_3$ | | | | 159 | oil | C$_{22}$H$_{21}$Cl$_2$F$_2$N$_3$O$_6$ | | | |
| 109 | 151–152 | C$_{18}$H$_{16}$ClF$_3$N$_3$O$_4$S | C 45.33 | 3.38 | 11.75 | 160 | oil | C$_{23}$H$_{23}$Cl$_2$F$_2$N$_3$O$_6$ | | | |
| | | | F 45.95 | 3.80 | 11.20 | 161 | oil | C$_{23}$H$_{26}$Cl$_2$F$_2$N$_4$O$_5$ | | | |
| 110 | oil | C$_{20}$H$_{16}$Cl$_2$F$_3$N$_3$O$_5$ | | | | 162 | oil | C$_{31}$H$_{42}$Cl$_2$F$_2$N$_4$O$_5$ | | | |

-continued

| Cmpd No. | M.P. (°C.) | Empirical Formula | Elemental Analysis | | |
|---|---|---|---|---|---|
| | | | C | H | N |
| 163 | 98-100 | $C_{22}H_{21}Cl_2F_2N_3O_5$ | | | |
| 164 | oil | $C_{24}H_{25}Cl_2F_2N_3O_7$ | | | |
| 165 | oil | $C_{23}H_{23}Cl_2F_2N_3O_5$ | | | |
| 166 | oil | $C_{24}H_{24}ClF_4N_3O_7$ | | | |
| 167 | 115-117 | $C_{19}H_{16}Cl_2F_2N_4O_4$ | | | |
| 168 | oil | $C_{24}H_{24}ClF_2N_3O_7$ | | | |
| 169 | oil | $C_{22}H_{21}ClF_3N_3O_6$ | | | |
| 170 | oil | $C_{24}H_{25}ClF_3N_3O_7$ | | | |
| 171 | 137 | $C_{17}H_{14}ClF_3N_3O_3$ | | | |
| 172 | 86-88 | $C_{24}H_{23}Cl_2F_2N_3O_5$ | | | |
| 173 | 113-114 | $C_{23}H_{24}Cl_2F_2N_4O_4$ | | | |
| 174 | 43-45 | $C_{37}H_{51}Cl_2F_2N_3O_5$ | | | |
| 175 | oil | $C_{24}H_{25}Cl_2F_2N_3O_5$ | | | |
| 176 | oil | $C_{17}H_{14}ClF_3N_3O_3$ | | | |
| 177 | 90-92 | $C_{19}H_{17}F_2N_3O_5$ | | | |
| 178 | 68-69 | $C_{16}H_{11}Cl_{12}F_2N_3O_3$ | | | |
| 179 | 100-101 | $C_{20}H_{17}Cl_2F_2N_3O_4S$ | | | |

TABLE 2A

| Cmpd No. | M.P. (°C.) | Empirical Formula | | Elemental Analysis | | |
|---|---|---|---|---|---|---|
| | | | | C | H | N |
| A1 | 120-123 | $C_{15}H_9ClF_3N_5O_4$ | C | 43.34 | 2.18 | 16.85 |
| | | | F | 43.52 | 2.35 | 16.82 |
| A2 | 138-140 | $C_{15}H_{11}ClF_3N_5O_2$ | | | | |
| A3 | 183-185 | $C_{21}H_{14}Cl_2F_3N_5O_4S$ | C | 45.01 | 2.52 | 12.50 |
| | | | F | 44.77 | 2.58 | 11.93 |
| A4 | 167-168 | $C_{17}H_{15}ClF_3N_5O_4S$ | C | 42.73 | 3.16 | 14.66 |
| | | | F | 42.41 | 3.00 | 14.29 |
| A5 | 179-181 | $C_{15}H_{10}ClF_3N_4O_3$ | C | 46.59 | 2.61 | 14.49 |
| | | | F | 46.42 | 2.48 | 14.25 |
| A6 | oil | $C_{19}H_{16}ClF_3N_4O_5$ | C | 48.26 | 3.41 | 11.85 |
| | | | F | 48.33 | 3.54 | 11.09 |
| A7 | oil | $C_{20}H_{18}ClF_3N_4O_5$ | C | 49.34 | 3.73 | 11.51 |
| | | | F | 49.16 | 3.65 | 10.82 |
| A8 | oil | $C_{22}H_{22}ClF_3N_4O_5$ | | | | |
| A9 | oil | $C_{21}H_{20}ClF_3N_4O_5$ | C | 50.35 | 4.03 | 11.19 |
| | | | F | 50.10 | 3.75 | 11.25 |
| A10 | 49-51 | $C_{18}H_{14}ClF_3N_4O_5$ | | | | |
| A11 | oil | $C_{18}H_{12}ClF_3N_4O_3$ | C | 50.90 | 2.85 | 13.19 |
| | | | F | 50.07 | 2.50 | 13.05 |
| A12 | 120-122 | $C_{17}H_{12}ClF_3N_4O_4$ | C | 47.62 | 2.82 | 13.07 |
| | | | F | 47.16 | 3.04 | 13.04 |

TABLE 3

Preemergence Herbicidal Activity

| | Compound No. | | | | | | | | | | | | | | |
|---|---|---|---|---|---|---|---|---|---|---|---|---|---|---|---|
| | 1 | 2 | 3 | 4 | 5 | 6 | 7 | 27 | 29 | 32 | 43 | 44 | 46 | 49 | 54 |
| | Rate (kg/ha) | | | | | | | | | | | | | | |
| Species | 8.0 %C | 4.0 %C | 4.0 %C | 4.0 %C | 4.0 %C | 0.5 %C | 0.5 %C | 0.25 %C | 0.25 %C | 0.125 %C | 0.25 %C | 0.25 %C | 0.125 %C | 0.125 %C | 0.25 %C |
| Cotton | 10 | 70 | 10 | 0 | 70 | 10 | 50 | 10 | 10 | 10 | 100 | 60 | 0 | 10 | 50 |
| Soybean | 10 | 100 | 80 | 10 | 70 | 30 | 90 | 50 | 10 | 10 | 90 | 20 | 20 | 0 | 20 |
| Corn | 50 | 85 | 60 | 20 | 60 | 10 | 95 | 80 | 90 | 10 | 100 | 50 | 5 | 0 | 100 |
| Rice | 0 | 95 | 60 | 20 | 70 | 10 | 80 | 80 | 60 | 40 | 90 | 50 | 70 | 20 | 70 |
| Wheat | 20 | 100 | 60 | 10 | 80 | 10 | 95 | 95 | 70 | 10 | 95 | 10 | 5 | 0 | 50 |
| Morningglory | 20 | 90 | 70 | 10 | 100 | 40 | 100 | 100 | 90 | 80 | 100 | 100 | 50 | 70 | 100 |
| Wild Mustard | — | 100 | 100 | 70 | 100 | 40 | 100 | 100 | 100 | 70 | 100 | 100 | 30 | 10 | 100 |
| Velvetleaf | 80 | 100 | 100 | 80 | 100 | 80 | 100 | 100 | 100 | 100 | 100 | 100 | 80 | 100 | 100 |
| Barnyardgrass | 90 | 100 | 95 | 30 | 100 | 95 | 95 | 100 | 100 | 0 | 100 | 90 | 90 | 20 | 100 |
| Green Foxtail | 50 | 100 | 100 | 70 | 100 | 100 | 100 | 100 | 100 | 100 | 100 | 100 | 90 | 10 | 100 |
| Johnsongrass | 0 | 85 | 100 | 70 | 100 | 40 | 95 | 100 | 95 | 10 | 95 | 70 | 20 | 40 | 100 |

| | Compound No. | | | | | | | | | | | | | | |
|---|---|---|---|---|---|---|---|---|---|---|---|---|---|---|---|
| | 55 | 56 | 66 | 82 | 91 | 92 | 93 | 94 | 95 | 96 | 97 | 98 | 99 | 100 | 101 |
| | Rate (kg/ha) | | | | | | | | | | | | | | |
| Species | 0.0313 %C | 0.25 %C | 0.25 %C | 0.125 %C | 0.0625 %C | 2.0 %C | 2.0 %C | 2.0 %C | 2.0 %C | 0.125 %C | 2.0 %C | 4.0 %C | 0.25 %C | 0.25 %C | 0.25 %C |
| Cotton | 50 | 100 | 0 | 5 | 5 | 0 | 5 | 0 | 0 | 50 | 5 | 0 | 0 | 0 | 80 |
| Soybean | 0 | 10 | 5 | 5 | 0 | 0 | 20 | 5 | 0 | 20 | 20 | 40 | 5 | 0 | 20 |
| Corn | 5 | 0 | 5 | 5 | 5 | 10 | 5 | 10 | 0 | 5 | 40 | 20 | 0 | 0 | 60 |
| Rice | 40 | 50 | 10 | 20 | 5 | 5 | 10 | 10 | 10 | 50 | 50 | 5 | 20 | 5 | 60 |
| Wheat | 0 | 10 | 0 | 0 | 0 | 10 | 5 | 10 | 20 | 50 | 10 | 0 | 10 | 0 | 10 |
| Morningglory | 10 | 90 | 20 | 20 | 50 | 10 | 0 | 0 | 0 | 70 | 20 | 10 | 30 | 10 | 95 |
| Wild Mustard | 80 | 30 | 0 | 10 | 95 | 0 | 10 | 10 | 20 | 80 | 0 | 80 | 60 | 50 | 100 |
| Velvetleaf | 80 | 90 | 20 | 80 | 100 | 0 | 0 | 0 | 0 | 100 | 40 | 80 | 20 | 10 | 100 |
| Barnyardgrass | 0 | 70 | 0 | 0 | 0 | 80 | 50 | 0 | 0 | 20 | 95 | 30 | 20 | 20 | 95 |
| Green Foxtail | 5 | 90 | 5 | 70 | 80 | 100 | 90 | 10 | 10 | 100 | 100 | 95 | 60 | 50 | 100 |
| Johnsongrass | 30 | 70 | 0 | 20 | 40 | 50 | 30 | 50 | 10 | 70 | 70 | 40 | 30 | 30 | 90 |

| | Compound No. | | | | | | | | | | | | | | |
|---|---|---|---|---|---|---|---|---|---|---|---|---|---|---|---|
| | 102 | 103 | 104 | 105 | 106 | 107 | 108 | 109 | 110 | 111 | 112 | 113 | 114 | 115 | 116 |
| | Rate (kg/ha) | | | | | | | | | | | | | | |
| Species | 2.0 %C | 2.0 %C | 1.0 %C | 2.0 %C | 2.0 %C | 2.0 %C | 2.0 %C | 0.5 %C | 0.25 %C | 2.0 %C | 0.25 %C | 0.25 %C | 0.25 %C | 0.25 %C | 0.25 %C |
| Cotton | 0 | 0 | 5 | 40 | 0 | 40 | 30 | 10 | 20 | 10 | 100 | 100 | 95 | 100 | 100 |
| Soybean | 0 | 0 | 20 | 60 | 40 | 100 | 70 | 10 | 10 | 0 | 10 | 0 | 10 | 10 | 0 |
| Corn | 0 | 0 | 70 | 30 | 30 | 20 | 40 | 5 | 40 | 5 | 20 | 5 | 20 | 10 | 0 |
| Rice | 5 | 0 | 60 | 70 | 50 | 50 | 50 | 30 | 40 | 40 | 70 | 50 | 60 | 40 | 5 |
| Wheat | 0 | 0 | 20 | 95 | 80 | 80 | 95 | 40 | 10 | 20 | 40 | 50 | 70 | 10 | 20 |
| Morningglory | 0 | 0 | 95 | 80 | 80 | 50 | 100 | 10 | 30 | 30 | 80 | 100 | 80 | 90 | 5 |
| Wild Mustard | 0 | 0 | 100 | 10 | 10 | 100 | 100 | 100 | 20 | 0 | 100 | 100 | 95 | 95 | 0 |
| Velvetleaf | 0 | 0 | 100 | 50 | 80 | 100 | 100 | 90 | 100 | 90 | 100 | 100 | 100 | 100 | 50 |
| Barnyardgrass | 0 | 0 | 100 | 100 | 70 | 90 | 100 | 60 | 30 | 90 | 80 | 95 | 100 | 50 | 10 |
| Green Foxtail | 0 | 0 | 100 | 100 | 95 | 100 | 100 | 80 | 100 | 90 | 100 | 100 | 100 | 100 | 20 |
| Johnsongrass | 0 | 0 | 95 | 50 | 20 | 30 | 95 | 50 | 20 | 70 | 100 | 100 | 100 | 90 | 10 |

TABLE 3-continued

Preemergence Herbicidal Activity

| | Compound No. | | | | | | | | | | | | | | |
|---|---|---|---|---|---|---|---|---|---|---|---|---|---|---|---|
| | 117 | 118 | 119 | 120 | 121 | 122 | 123 | 124 | 125 | 126 | 127 | 128 | 129 | 130 | 131 |
| | Rate (kg/ha) | | | | | | | | | | | | | | |
| Species | 0.0313 %C | 2.0 %C | 2.0 %C | 2.0 %C | 2.0 %C | 1.0 %C | 1.0 %C | 0.125 %C | 8.0 %C | 2.0 %C | 2.0 %C | 2.0 %C | 2.0 %C | 2.0 %C | 2.0 %C |
| Cotton | 50 | 0 | 10 | 50 | 0 | 10 | 5 | 30 | — | 80 | 80 | 90 | 95 | 90 | 50 |
| Soybean | 0 | 5 | 5 | 10 | 10 | 0 | 5 | 0 | 20 | 30 | 50 | 40 | 100 | 30 | 80 |
| Corn | 20 | 10 | 5 | 0 | 0 | 20 | 10 | 0 | 20 | 70 | 95 | 20 | 100 | 100 | 80 |
| Rice | 10 | 20 | 10 | 10 | 10 | 30 | 20 | 30 | — | 70 | 80 | 40 | 100 | 60 | 80 |
| Wheat | 0 | 5 | 0 | 20 | 5 | 10 | 5 | 10 | 100 | 10 | 30 | 10 | 95 | 50 | 60 |
| Morningglory | 10 | 10 | 60 | 95 | 70 | 80 | 0 | 100 | 70 | 80 | 70 | 90 | 100 | 100 | 80 |
| Wild Mustard | 80 | 0 | 60 | 10 | 0 | 40 | 0 | 40 | — | 95 | 80 | 100 | 100 | 100 | 100 |
| Velvetleaf | 80 | 20 | 100 | 100 | 90 | 95 | 70 | 100 | 95 | 100 | 100 | 100 | 100 | 100 | 100 |
| Barnyardgrass | 30 | 50 | 20 | 95 | 50 | 100 | 60 | 80 | 90 | 100 | 100 | 80 | 100 | 100 | 100 |
| Green Foxtail | 30 | 80 | 100 | 100 | 95 | 100 | 30 | 80 | 100 | 95 | 100 | 80 | 100 | 100 | 100 |
| Johnsongrass | 10 | 50 | 40 | 70 | 40 | 90 | 20 | 70 | — | 80 | 80 | 80 | 100 | 100 | 100 |

| | Compound No. | | | | | | | | | | | |
|---|---|---|---|---|---|---|---|---|---|---|---|---|
| | 132 | 145 | 146 | 147 | 148 | 149 | 150 | 151 | 152 | 153 | 154 | 155 | 156 |
| | Rate (kg/ha) | | | | | | | | | | | |
| Species | 8.0 %C | 0.0625 %C | 0.0625 %C | 0.25 %C | 0.0625 %C | 0.125 %C | 0.125 %C | 0.125 %C | 0.125 %C | 0.125 %C | 0.125 %C | 0.25 %C | 0.25 %C |
| Cotton | — | 15 | 40 | 0 | 50 | 5 | 30 | 0 | 15 | 10 | 50 | 80 | 70 |
| Soybean | 0 | 20 | 15 | 0 | 70 | 50 | 15 | 5 | 5 | 10 | 50 | 90 | 60 |
| Corn | 0 | 30 | 10 | 10 | 15 | 10 | 5 | 0 | 5 | 15 | 5 | 70 | 60 |
| Rice | — | 40 | 30 | 10 | 10 | 40 | 60 | 0 | 80 | 20 | 95 | 95 | 90 |
| Wheat | 0 | 30 | 0 | 0 | 5 | 0 | 10 | 0 | 5 | 5 | 15 | 40 | 60 |
| Morningglory | 0 | 70 | 95 | 70 | 70 | 70 | 80 | 70 | 20 | 30 | 100 | 100 | 100 |
| Wild Mustard | — | 95 | 100 | 0 | 95 | 95 | 95 | 0 | 70 | 0 | 95 | 100 | 100 |
| Velvetleaf | 0 | 100 | 100 | 50 | 100 | 90 | 100 | 5 | 90 | 50 | 90 | 100 | 100 |
| Barnyardgrass | 0 | 50 | 60 | 10 | 40 | 20 | 50 | 5 | 5 | 0 | 20 | 70 | 90 |
| Green Foxtail | 0 | 100 | 100 | 70 | 100 | 100 | 100 | 0 | 60 | 50 | 90 | 95 | 100 |
| Johnsongrass | — | 95 | 90 | 5 | 90 | 50 | 70 | 0 | 70 | 0 | 40 | 95 | 100 |

TABLE 3A

Preemergence Herbicidal Activity

| | Compound No. | | | | | | | | | | | |
|---|---|---|---|---|---|---|---|---|---|---|---|---|
| | A1 | A2 | A3 | A4 | A5 | A6 | A7 | A8 | A9 | A10 | A11 | A12 |
| | Rate (kg/ha) | | | | | | | | | | | |
| Species | 2.0 %C | 2.0 %C | 2.0 %C | 2.0 %C | 2.0 %C | 0.5 %C | 0.5 %C | 0.5 %C | 0.125 %C | 0.5 %C | 2.0 %C | 2.0 %C |
| Cotton | 30 | 10 | 40 | 50 | 20 | 100 | 100 | 20 | 20 | 70 | 60 | 10 |
| Soybean | 50 | 70 | 10 | 50 | 70 | 70 | 40 | 20 | 10 | 50 | 90 | 60 |
| Corn | 30 | 20 | 0 | 90 | 95 | 100 | 100 | 70 | 20 | 95 | 95 | 70 |
| Rice | 60 | 60 | 30 | 60 | 90 | 95 | 90 | 95 | 80 | 95 | 90 | 50 |
| Wheat | 90 | 80 | 30 | 70 | 95 | 95 | 95 | 40 | 30 | 95 | 95 | 80 |
| Morningglory | 80 | 80 | 50 | 90 | 95 | 100 | 100 | 90 | 100 | 100 | 100 | 80 |
| Wild Mustard | 50 | 100 | 100 | 100 | 80 | 100 | 100 | 95 | 20 | 100 | 100 | 70 |
| Velvetleaf | 100 | 100 | 100 | 100 | 100 | 100 | 100 | 90 | 90 | 100 | 100 | 100 |
| Barnyardgrass | 60 | 70 | 40 | 100 | 100 | 100 | 100 | 95 | 30 | 100 | 100 | 100 |
| Green Foxtail | 100 | 100 | 100 | 100 | 100 | 100 | 100 | 100 | 50 | 100 | 100 | 100 |
| Johnsongrass | 95 | 70 | 30 | 95 | 80 | 100 | 100 | 95 | 90 | 100 | 100 | 80 |

TABLE 3B

Preemergence Herbicidal Activity

| | Compound No. | |
|---|---|---|
| | B89 | B90 |
| | Rate (kg/ha) | |
| Species | 0.25 %C | 0.125 %C |
| Cotton | — | — |
| Soybean | 0 | 10 |
| Corn | 25 | 10 |
| Rice | — | — |
| Wheat | 0 | 0 |
| Morningglory | 60 | 5 |
| Wild Mustard | — | — |
| Velvetleaf | 100 | 100 |
| Barnyardgrass | — | — |
| Green Foxtail | 80 | 0 |
| Johnsongrass | 30 | 0 |

TABLE 3C

Preemergence Herbicidal Activity

| | Compound No. | |
|---|---|---|
| | C89* | C90* |
| | Rate (kg/ha) | |
| Species | 0.125 %C | 0.125 %C |
| Cotton | — | — |
| Soybean | 0 | 0 |
| Corn | 10 | 15 |
| Rice | — | — |
| Wheat | 0 | 0 |
| Morningglory | 0 | 0 |
| Wild Mustard | 0 | 0 |
| Velvetleaf | — | — |
| Barnyardgrass | — | — |
| Green Foxtail | 0 | 0 |

TABLE 3C-continued

Preemergence Herbicidal Activity

| | Compound No. | |
|---|---|---|
| | C89* | C90* |
| | Rate (kg/ha) | |
| | 0.125 | 0.125 |
| Species | % C | % C |
| Johnsongrass | 0 | 30 |

*Z is NH

TABLE 4

Postemergence Herbicidal Activity

| | Compound No. | | | | | | | | | | | |
|---|---|---|---|---|---|---|---|---|---|---|---|---|
| | 1 | 2 | 3 | 4 | 5 | 6 | 7 | 27 | 29 | 32 | 43 | 44 |
| | Rate (kg/ha) | | | | | | | | | | | |
| | 8.0 | 4.0 | 4.0 | 4.0 | 4.0 | 0.5 | 0.5 | 0.25 | 0.25 | 0.125 | 0.0625 | 0.0625 |
| Species | % C | % C | % C | % C | % C | % C | % C | % C | % C | % C | % C | % C |
| Cotton | 60 | 100 | 95 | 70 | 100 | 95 | 100 | 100 | 100 | 100 | 90 | 100 |
| Soybean | 60 | 95 | 70 | 50 | 100 | 80 | 100 | 100 | 60 | 70 | 100 | 70 |
| Corn | 50 | 95 | 100 | 60 | 100 | 100 | 100 | 100 | 100 | 100 | 100 | 100 |
| Rice | 30 | 95 | 70 | 20 | 95 | 60 | 100 | 80 | 40 | 50 | 90 | 10 |
| Wheat | 20 | 100 | 95 | 20 | 100 | 95 | 100 | 95 | 95 | 30 | 100 | 100 |
| Morningglory | 60 | 100 | 100 | 90 | 100 | 100 | 100 | 100 | 100 | 100 | 100 | 100 |
| Wild Mustard | — | 70 | 95 | 70 | 100 | 95 | 100 | 100 | 100 | 100 | 100 | 100 |
| Velvetleaf | 100 | 100 | 100 | 100 | 100 | 100 | 100 | 100 | 100 | 100 | 100 | 100 |
| Barnyardgrass | 40 | 100 | 95 | 30 | 100 | 90 | 100 | 100 | 100 | 100 | 100 | 95 |
| Green Foxtail | 80 | 95 | 100 | 30 | 100 | 95 | 100 | 100 | 100 | 100 | 95 | 100 |
| Johnsongrass | 30 | 95 | 85 | 30 | 100 | 95 | 100 | 100 | 95 | 100 | 100 | 80 |

| | Compound No. | | | | | | | | | | | |
|---|---|---|---|---|---|---|---|---|---|---|---|---|
| | 46 | 49 | 54 | 55 | 56 | 66 | 82 | 91 | 92 | 93 | 94 | 95 |
| | Rate (kg/ha) | | | | | | | | | | | |
| | 0.125 | 0.125 | 0.25 | 0.0313 | 0.25 | 0.25 | 0.125 | 0.0625 | 2.0 | 2.0 | 2.0 | 2.0 |
| Species | % C | % C | % C | % C | % C | % C | % C | % C | % C | % C | % C | % C |
| Cotton | 80 | 100 | 100 | 100 | 100 | 80 | 100 | 100 | 60 | 90 | 30 | 80 |
| Soybean | 70 | 95 | 90 | 100 | 80 | 60 | 70 | 70 | 10 | 50 | 30 | 30 |
| Corn | 70 | 100 | 100 | 100 | 100 | 50 | 100 | 100 | 100 | 30 | 40 | 30 |
| Rice | 40 | 80 | 70 | 50 | 50 | 10 | 40 | 50 | 20 | 20 | 20 | 20 |
| Wheat | 40 | 100 | 95 | 95 | 90 | 50 | 80 | 90 | 20 | 30 | 20 | 10 |
| Morningglory | 100 | 100 | 100 | 100 | 100 | 100 | 100 | 100 | 40 | 100 | 30 | 60 |
| Wild Mustard | 100 | 90 | 100 | 100 | 100 | 30 | 50 | 100 | 20 | 100 | 30 | 10 |
| Velvetleaf | 100 | 100 | 100 | 100 | 100 | 100 | 100 | 100 | 90 | 100 | 90 | 60 |
| Barnyardgrass | 80 | 100 | 100 | 95 | 100 | 50 | 100 | 95 | 20 | 30 | 20 | 10 |
| Green Foxtail | 100 | 100 | 100 | 100 | 100 | 30 | 100 | 100 | 70 | 95 | 30 | 30 |
| Johnsongrass | 100 | 100 | 100 | 95 | 90 | 50 | 100 | 90 | 30 | 30 | 30 | 30 |

| | Compound No. | | | | | | | | | | | |
|---|---|---|---|---|---|---|---|---|---|---|---|---|
| | 96 | 97 | 98 | 99 | 100 | 101 | 102 | 103 | 104 | 105 | 106 | 107 |
| | Rate (kg/ha) | | | | | | | | | | | |
| | 0.125 | 2.0 | 4.0 | 0.0625 | 0.0625 | 0.0625 | 2.0 | 2.0 | 1.0 | 2.0 | 2.0 | 2.0 |
| Species | % C | % C | % C | % C | % C | % C | % C | % C | % C | % C | % C | % C |
| Cotton | 100 | 80 | 50 | 80 | 100 | 100 | 5 | 5 | 100 | 100 | 80 | 95 |
| Soybean | 90 | 60 | 40 | 30 | 40 | 30 | 0 | 10 | 80 | 70 | 80 | 95 |
| Corn | 100 | 30 | 70 | 30 | 40 | 50 | 10 | 40 | 100 | 95 | 80 | 100 |
| Rice | 70 | 20 | 70 | 5 | 0 | 10 | 10 | 5 | 60 | 50 | 40 | 50 |
| Wheat | 50 | 30 | 30 | 20 | 20 | 10 | 5 | 10 | 50 | 70 | 80 | 95 |
| Morningglory | 100 | 20 | 80 | 50 | 30 | 90 | 10 | 40 | 100 | 80 | 100 | 100 |
| Wild Mustard | 100 | 30 | 70 | 10 | 10 | 60 | 10 | 20 | 100 | 100 | 20 | 100 |
| Velvetleaf | 100 | 100 | 95 | 90 | 100 | 90 | 10 | 40 | 100 | 100 | 100 | 100 |
| Barnyardgrass | 100 | 20 | 50 | 30 | 20 | 30 | 10 | 30 | 100 | 95 | 70 | 95 |
| Green Foxtail | 100 | 70 | 80 | 50 | 10 | 20 | 10 | 20 | 100 | 100 | 100 | 100 |
| Johnsongrass | 100 | 40 | 40 | 30 | 20 | 60 | 10 | 20 | 90 | 50 | 50 | 80 |

| | Compound No. | | | | | | | | | | | |
|---|---|---|---|---|---|---|---|---|---|---|---|---|
| | 108 | 109 | 110 | 111 | 112 | 113 | 114 | 115 | 116 | 117 | 118 | 119 |
| | Rate (kg/ha) | | | | | | | | | | | |
| | 2.0 | 0.5 | 0.25 | 2.0 | 0.25 | 0.25 | 0.25 | 0.25 | 0.25 | 0.0313 | 2.0 | 2.0 |
| Species | % C | % C | % C | % C | % C | % C | % C | % C | % C | % C | % C | % C |
| Cotton | 95 | 95 | 100 | 100 | 100 | 100 | 100 | 95 | 80 | 100 | 80 | 95 |
| Soybean | 90 | 50 | 50 | 60 | 90 | 95 | 80 | 80 | 40 | 60 | 40 | 40 |
| Corn | 80 | 50 | 100 | 100 | 100 | 100 | 100 | 90 | 95 | 100 | 50 | 100 |
| Rice | 60 | 50 | 60 | 50 | 70 | 70 | 70 | 70 | 40 | 40 | 20 | 50 |
| Wheat | 95 | 60 | 95 | 50 | 100 | 90 | 95 | 95 | 95 | 95 | 30 | 50 |
| Morningglory | 100 | 95 | 100 | 70 | 100 | 100 | 100 | 100 | 95 | 100 | 50 | 100 |
| Wild Mustard | 100 | 100 | 100 | 100 | 100 | 100 | 100 | 100 | 90 | 100 | 0 | 80 |
| Velvetleaf | 100 | 100 | 100 | 100 | 100 | 100 | 100 | 100 | 100 | 100 | 100 | 100 |
| Barnyardgrass | 100 | 60 | 100 | 95 | 100 | 100 | 100 | 100 | 90 | 95 | 40 | 90 |
| Green Foxtail | 100 | 70 | 100 | 100 | 100 | 100 | 100 | 100 | 95 | 95 | 40 | 100 |
| Johnsongrass | 80 | 50 | 100 | 95 | 100 | 100 | 100 | 95 | 80 | 90 | 70 | 100 |

| | Compound No. | | | | | | | | | | | |
|---|---|---|---|---|---|---|---|---|---|---|---|---|
| | 120 | 121 | 122 | 123 | 124 | 125 | 126 | 127 | 128 | 129 | 130 | 131 | 132 |
| | Rate (kg/ha) | | | | | | | | | | | | |
| | 2.0 | 2.0 | 1.0 | 1.0 | 0.125 | 8.0 | 2.0 | 2.0 | 2.0 | 2.0 | 2.0 | 2.0 | 8.0 |

TABLE 4-continued

Postemergence Herbicidal Activity

| Species | % C | % C | % C | % C | % C | % C | % C | % C | % C | % C | % C | % C | % C |
|---|---|---|---|---|---|---|---|---|---|---|---|---|---|
| Cotton | 100 | 100 | 90 | 100 | 100 | — | 100 | 100 | 100 | 100 | 100 | 100 | — |
| Soybean | 80 | 50 | 50 | 50 | 95 | 50 | 90 | 60 | 90 | 100 | 90 | 80 | 10 |
| Corn | 100 | 100 | 100 | 70 | 100 | 60 | 100 | 100 | 70 | 100 | 100 | 100 | 10 |
| Rice | 95 | 70 | 50 | 70 | 95 | — | 50 | 40 | 40 | 100 | 90 | 50 | — |
| Wheat | 40 | 50 | 40 | 40 | 95 | 40 | 70 | 40 | 50 | 100 | 100 | 95 | 10 |
| Morningglory | 100 | 95 | 90 | 50 | 100 | 100 | 95 | 95 | 100 | 100 | 100 | 100 | 10 |
| Wild Mustard | 40 | 95 | 100 | 40 | 100 | — | 100 | 100 | 100 | 100 | 100 | 100 | — |
| Velvetleaf | 100 | 100 | 100 | 100 | 100 | 100 | 100 | 100 | 100 | 100 | 100 | 100 | 10 |
| Barnyardgrass | 95 | 90 | 100 | 95 | 100 | 20 | 100 | 100 | 95 | 100 | 100 | 90 | 20 |
| Green Foxtail | 100 | 100 | 100 | 50 | 100 | 90 | 100 | 100 | 95 | 100 | 100 | 100 | 0 |
| Johnsongrass | 95 | 95 | 95 | 50 | 100 | — | 90 | 80 | 60 | 100 | 100 | 90 | — |

| | Compound No. | | | | | | | | | | |
|---|---|---|---|---|---|---|---|---|---|---|---|
| | 145 | 146 | 147 | 148 | 149 | 150 | 151 | 152 | 153 | 154 | 155 |
| | Rate (kg/ha) | | | | | | | | | | |
| Species | 0.0625 % C | 0.0625 % C | 0.25 % C | 0.0625 % C | 0.125 % C | 0.125 % C | 0.125 % C | 0.125 % C | 0.125 % C | 0.125 % C | 0.25 % C |
| Cotton | 100 | 100 | 60 | 100 | 100 | 100 | 70 | 100 | 90 | 100 | 100 |
| Soybean | 100 | 95 | 60 | 60 | 50 | 90 | 50 | 90 | 40 | 80 | 95 |
| Field Corn | 100 | 100 | 100 | 100 | 100 | 100 | 85 | 100 | 100 | 100 | 100 |
| Rice | 70 | 60 | 15 | 60 | 40 | 60 | 5 | 15 | 40 | 20 | 85 |
| Wheat | 95 | 95 | 30 | 90 | 95 | 85 | 30 | 95 | 30 | 100 | 100 |
| Morningglory | 100 | 100 | 100 | 100 | 100 | 100 | 100 | 100 | 95 | 100 | 100 |
| Wild Mustard | 100 | 100 | 70 | 100 | 70 | 95 | 30 | 100 | 0 | 100 | 100 |
| Velvetleaf | 100 | 100 | 70 | 100 | 100 | 100 | 20 | 100 | 100 | 100 | 100 |
| Barnyardgrass | 95 | 90 | 15 | 70 | 80 | 95 | 40 | 70 | 10 | 95 | 100 |
| Green Foxtail | 70 | 95 | 80 | 100 | 90 | 100 | 50 | 100 | 50 | 100 | 100 |
| Johnsongrass | 60 | 90 | 30 | 60 | 80 | 95 | 70 | 95 | 50 | 95 | 100 |

| | Compound No. | | | | | | |
|---|---|---|---|---|---|---|---|
| | 156 | 157 | 158 | 159 | 160 | 161 | 162 |
| | Rate (kg/ha) | | | | | | |
| Species | 0.25 % C | 0.25 % C | 0.25 % C | 0.125 % C | 0.125 % C | 0.125 % C | 0.125 % C |
| Cotton | 100 | 100 | 100 | 100 | 100 | 100 | 100 |
| Soybean | 95 | 85 | 95 | 75 | 70 | 75 | 60 |
| Field Corn | 100 | 100 | 100 | 100 | 100 | 100 | 90 |
| Rice | 90 | 30 | 50 | 40 | 20 | 15 | 10 |
| Wheat | 100 | 95 | 100 | 100 | 100 | 100 | 100 |
| Morningglory | 100 | 100 | 100 | 100 | 80 | 60 | 10 |
| Wild Mustard | 90 | 100 | 100 | 20 | 30 | 30 | 60 |
| Velvetleaf | 100 | 100 | 100 | 100 | 100 | 0 | 90 |
| Barnyardgrass | 70 | 95 | 100 | 80 | 90 | 60 | 60 |
| Green Foxtail | 100 | 100 | 100 | — | — | — | — |
| Johnsongrass | 95 | 70 | 90 | 95 | 90 | 70 | 70 |

TABLE 4A

Postemergence Herbicidal Activity

| | Compound No. | | | | | | | | | | | |
|---|---|---|---|---|---|---|---|---|---|---|---|---|
| | A1 | A2 | A3 | A4 | A5 | A6 | A7 | A8 | A9 | A10 | A11 | A12 |
| | Rate (kg/ha) | | | | | | | | | | | |
| Species | 2.0 % C | 2.0 % C | 2.0 % C | 2.0 % C | 2.0 % C | 0.5 % C | 0.5 % C | 0.5 % C | 0.125 % C | 0.5 % C | 2.0 % C | 2.0 % C |
| Cotton | 100 | 100 | 80 | 50 | 100 | 100 | 100 | 100 | 95 | 95 | 100 | 100 |
| Soybean | 40 | 90 | 80 | 95 | 95 | 100 | 95 | 80 | 70 | 70 | 95 | 95 |
| Corn | 60 | 70 | 40 | 100 | 70 | 100 | 100 | 100 | 100 | 100 | 100 | 80 |
| Rice | 10 | 90 | 50 | 95 | 70 | 70 | 90 | 100 | 70 | 100 | 80 | 80 |
| Wheat | 40 | 90 | 60 | 100 | 90 | 95 | 100 | 95 | 100 | 90 | 80 | 70 |
| Morningglory | 100 | 100 | 100 | 100 | 90 | 100 | 100 | 100 | 100 | 100 | 100 | 100 |
| Wild Mustard | 80 | 80 | 100 | 100 | 90 | 90 | 90 | 100 | 50 | 80 | 100 | 95 |
| Velvetleaf | 100 | 100 | 100 | 100 | 100 | 100 | 100 | 100 | 100 | 100 | 100 | 100 |
| Barnyardgrass | 70 | 90 | 60 | 95 | 100 | 100 | 100 | 100 | 100 | 100 | 100 | 95 |
| Green Foxtail | 100 | 100 | 100 | 100 | 100 | 100 | 95 | 100 | 95 | 100 | 100 | 95 |
| Johnsongrass | 70 | 80 | 40 | 70 | 40 | 95 | 100 | 95 | 90 | 100 | 95 | 0 |

TABLE 4B

| | Postemergence Herbicidal Activity | |
|---|---|---|
| | Compound No. | |
| | B89 | B90 |
| | Rate (kg/ha) | |
| | 0.25 | 0.125 |
| Species | % C | % C |
| Cotton | — | — |
| Soybean | 90 | 60 |
| Corn | 35 | 15 |
| Rice | — | — |
| Wheat | 80 | 40 |
| Morningglory | 100 | 100 |
| Wild Mustard | — | — |
| Velvetleaf | 100 | 100 |
| Barnyardgrass | — | — |
| Green Foxtail | 100 | 50 |
| Johnsongrass | 90 | 30 |

TABLE 4C

| | Postemergence Herbicidal Activity | |
|---|---|---|
| | Compound No. | |
| | C89* | C90* |
| | Rate (kg/ha) | |
| | 0.125 | 0.125 |
| Species | % C | % C |
| Cotton | — | — |
| Soybean | 0 | 20 |
| Corn | 0 | 35 |
| Rice | — | — |
| Wheat | 0 | 10 |
| Morningglory | 0 | 50 |
| Wild Mustard | 10 | 0 |
| Velvetleaf | — | — |
| Barnyardgrass | — | — |
| Green Foxtail | 10 | 40 |
| Johnsongrass | 0 | 10 |

*Z is NH

I claim:

1. An herbicidal compound of the formula

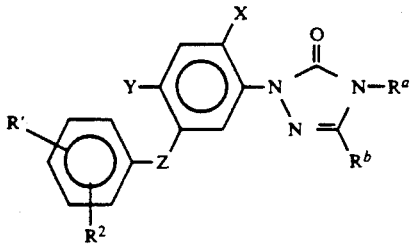

in which X is halogen, alkyl, haloalkyl or nitro; Y is halogen, alkyl, alkoxy, alkylthio, haloalkyl, nitro, cyano, alkylsulfonylalkyl, —SOCF$_3$, or halo lower alkoxy;

R$^a$ is lower haloalkyl, lower alkyl, alkenyl, or alkynyl;

R$^b$ is hydrogen, halogen, lower alkyl, lower haloalkyl, alkoxy, alkylsulfonyl, alkylthio or haloalkylsulfonyl;

R' is H, alkyl, halogen, haloalkyl, nitro, alkoxy, alkylthio or cyano;

R$^2$ is H, halogen, hydroxy, alkylcarbonyloxy, alkenyloxy, cyano, alkynyloxy, alkyl, haloalkyl, alkoxy, haloalkoxy, nitro, amino, alkylthio, —COOH, —COOR$^7$, —CONHSO$_2$R$^5$, —CONHR$^5$, —CONHOR$^7$, —COOCH(R$^4$)COR$^3$, —NHSO$_2$R$^7$, —N(SO$_2$R$^7$)$_2$, —SCH(R$^4$)COR$^3$, —NHCH(R$^4$)COR$^3$, R$^3$[CO—CH—(R$^4$)—O—]$_n$— or NCCH(R$^4$)O—[CO—CH(R$^4$)—O]$_m$—;

provided that where R' is H, halogen, alkyl, or alkoxy, or R$^a$ is alkyl; R$^b$ is other than H or alkyl, or R$^2$ is other than H, halogen, alkyl, or alkoxy;

R$^3$ is OH, O$^-$ak$^+$, alkoxy, cycloaklyloxy, alkenyloxy, alkynyloxy, —O[CH(R$^8$)(CH$_2$)$_p$O]$_r$R$^9$, amino, arylamino, alkylamino, alkenylamino, alkoxyamino, alkylhaloalkyl- or arylsulfonylamino of the formula —NHSO$_2$R$^5$ or —N(SO$_2$R$^5$)SO$_2$R$^6$;

R$^4$ is H or CH$_3$;

R$^5$ and R$^6$ are independently alkyl, haloalkyl or aryl;

R$^7$ is lower alkyl; R$^8$ is H or CH$_3$; R$^9$ is alkyl;

n is 1 or 2;

p is 0 to 5;

m is zero or 1;

r is 1 to 6;

ak$^+$ is sodium, potassium, or ammonium;

Z is O, S, NH or alkylamino;

with the proviso that any cycloalkyl group has from 3 to 7 carbon atoms; any alkyl, alkenyl or alkynyl moiety in Z, R', R$_2$, R$_3$, R$_5$, R$_6$ or R$_9$ has 1 to 6 carbon atoms; and any aryl moiety thereof is phenyl, alkoxyphenyl or halophenyl.

2. A compound as in claim 1 in which R$^2$ is [—[OCH(R$^4$)$^{co}$]$_n$$^{R3}$] R$^3$[CO—CH—(R$^4$)—O—]$_n$— or [—[OCH(R$_4$)CO]$_m$—OCH(R$_4$)CN] NCCH(R$^4$)O—[CO—CH(R$^4$)—O]$_m$—.

3. A compound as in claim 2 in which n is 1 and m is zero.

4. A compound as in claim 1 in which R$^2$ is [—[OCH(R$^4$)CO]N$^{R3}$] R$^3$[CO—CH—(R$^4$)—O—]$_n$—.

5. A compound as in claim 4 in which X and Y are halogen, R$^b$ is methyl and R$^a$ is difluoromethyl.

6. A compound as in claim 5 in which X is chlorine, fluorine or bromine and Y is chlorine or bromine at its 4-position.

7. A compound as in claim 6 in which X is F.

8. A compound as in claim 7 in which Z is 0.

9. A compound as in claim 8 in which R$^4$ is methyl and n is one.

10. A compound as in claim 9 in which R$^2$ is para to Z.

11. A compound as in claim 10 in which R$^3$ is lower alkoxy.

12. A compound as in claim 11 in which R' is F or Cl and is ortho to Z.

13. A compound as in claim 12 in which R$^3$ is ethoxy and R' is F.

14. A compound as in claim 13 in which R$^3$ is methoxy and R' is F.

15. A compound of claim 1 in which R$^3$ is —O[(CH(R$^8$)(CH$_2$)$_p$O]$_r$R$^9$.

16. A compound of claim 15 in which R$^8$ is H, p is 1 and r is 2.

17. An herbicidal composition comprising an herbicidally effective amount of the compound of claim 1 in admixture with a suitable carrier.

18. A method for controlling undesired plant growth which comprises applying to the locus where control is desired an herbicidally effective amount of the composition of claim 17.

19. An herbicidal composition comprising an herbicidally effective amount of the compound of claim 4 in admixture with a suitable carrier.

20. A method for controlling undesired plant growth which comprises applying to the locus where control is desired an herbicidally effective amount of the composition of claim 19.

21. An herbicidal composition comprising an herbicidally effective amount of the compound of claim 15 in admixture with a suitable carrier.

22. A method for controlling undesired plant growth which comprises applying to the locus where control is desired an herbicidally effective amount of the composition of claim 21.

* * * * *